(12) United States Patent
Lang et al.

(10) Patent No.: US 7,856,980 B2
(45) Date of Patent: *Dec. 28, 2010

(54) FOREHEAD PAD FOR RESPIRATORY MASK

(75) Inventors: Bernd Christoph Lang, Grafelfing (DE); Timothy Tsun-Fai Fu, Carlingford (AU); Perry David Lithgow, Glenwood (AU); Memduh Guney, Killara (AU); Joanne Elizabeth Drew, Balgowlah Heights (AU); Martin Bechtel, Winsen/Luhe (DE); Achim Biener, Munich (DE); Michael Kassipillai Gunaratnam, Marsfield (AU); Aaron Samuel Davidson, Newport (AU); Milind Chandrakant Raje, Wentworthville (AU)

(73) Assignees: ResMed Limited, Bella Vista (AU); MAP Medizin-Technologie GmbH, Martinsried (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/705,451

(22) Filed: Feb. 13, 2007

(65) Prior Publication Data

US 2007/0157934 A1 Jul. 12, 2007

Related U.S. Application Data

(63) Continuation of application No. 10/655,595, filed on Sep. 5, 2003, now Pat. No. 7,216,647, which is a continuation-in-part of application No. 10/235,846, filed on Sep. 6, 2002, now Pat. No. 6,823,869.

(60) Provisional application No. 60/467,572, filed on May 5, 2003, provisional application No. 60/424,696, filed on Nov. 8, 2002, provisional application No. 60/342,854, filed on Dec. 28, 2001, provisional application No. 60/317,486, filed on Sep. 7, 2001.

(51) Int. Cl.
*A62B 18/08* (2006.01)
(52) U.S. Cl. ............... 128/206.27; 128/207.11
(58) Field of Classification Search ............ 128/201.22, 128/201.23, 201.24, 201.25, 201.28, 205.25, 128/205.27, 205.28, 206.12–206.15, 206.17–206.19, 128/206.21, 206.24, 206.25, 206.26–206.28, 128/207.11, 207.12, 207.13, 200.28, DIG. 26, 128/912, 201.11; 2/411, 426, 414, 424; D24/110.1, D24/110.5

See application file for complete search history.

(56) References Cited

U.S. PATENT DOCUMENTS 1,081,745 A 12/1913 Johnston (Continued)

FOREIGN PATENT DOCUMENTS

DE 29723101 U1 7/1998

(Continued)

OTHER PUBLICATIONS

PCT International Search Report dated Oct. 8, 2003.

(Continued)

*Primary Examiner*—Danton DeMille
(74) *Attorney, Agent, or Firm*—Nixon & Vanderhye P.C.

(57) ABSTRACT

A forehead pad for use in a respiratory mask with a forehead support, which includes a base portion to contact a user's forehead, a support post connected to the base portion, and a head adapted to connect the support post to a forehead support. A pair of forehead pads may be joined with a connector.

27 Claims, 27 Drawing Sheets

U.S. PATENT DOCUMENTS

| | | | |
|---|---|---|---|
| 4,676,241 | A | 6/1987 | Webb et al. |
| 4,713,844 | A | 12/1987 | Westgate |
| 4,944,310 | A | 7/1990 | Sullivan |
| 5,243,971 | A | 9/1993 | Sullivan et al. |
| 5,245,995 | A | 9/1993 | Sullivan et al. |
| 5,441,046 | A | 8/1995 | Starr et al. |
| 5,704,345 | A | 1/1998 | Berthon-Jones et al. |
| 5,921,239 | A | 7/1999 | McCall et al. |
| 6,112,746 | A | 9/2000 | Kwok et al. |
| 6,119,693 | A | 9/2000 | Kwok et al. |
| 6,347,631 | B1 | 2/2002 | Hansen et al. |
| 6,388,640 | B1 | 5/2002 | Chigira et al. |
| 6,412,487 | B1 | 7/2002 | Gunaratnam et al. |
| 6,422,238 | B1 | 7/2002 | Lithgow |
| 6,427,694 | B1 | 8/2002 | Hecker et al. |
| 6,463,931 | B1 | 10/2002 | Kwok et al. |
| 6,467,483 | B1 | 10/2002 | Kopacko et al. |
| 6,520,182 | B1 | 2/2003 | Gunaratnam |
| 6,530,373 | B1 | 3/2003 | Patron et al. |
| 6,536,435 | B1 | 3/2003 | Fecteau et al. |
| D484,237 | S | 12/2003 | Lang et al. |
| 6,823,869 | B2 | 11/2004 | Raje et al. |
| 6,832,615 | B2 * | 12/2004 | Hensel ........................ 132/321 |
| D502,260 | S | 2/2005 | Lang et al. |
| 6,986,352 | B2 | 1/2006 | Frater et al. |
| D515,698 | S | 2/2006 | Lang et al. |
| 7,000,614 | B2 | 2/2006 | Lang et al. |
| 7,059,326 | B2 * | 6/2006 | Heidmann et al. ..... 128/207.11 |
| 7,100,610 | B2 | 9/2006 | Biener |
| 2003/0062048 | A1 | 4/2003 | Gradon et al. |
| 2004/0112387 | A1 | 6/2004 | Lang et al. |
| 2005/0011522 | A1 * | 1/2005 | Ho et al. ................. 128/206.21 |
| 2005/0199239 | A1 | 9/2005 | Lang et al. |
| 2005/0211252 | A1 | 9/2005 | Lang et al. |

FOREIGN PATENT DOCUMENTS

| | | |
|---|---|---|
| DE | 200 17 940 UI | 2/2001 |
| DE | 100 45 183 A1 | 5/2002 |
| DE | 100 51 891 A1 | 5/2002 |
| DE | 10045183 A1 * | 5/2002 |
| EP | 1 205 205 | 5/2002 |
| JP | 9-292588 | 11/1997 |
| WO | WO 98/12965 | 4/1998 |
| WO | WO 99/61088 | 12/1999 |
| WO | WO 00/78384 | 12/2000 |
| WO | WO 02/32491 A2 | 4/2002 |
| WO | WO 03/035156 A2 | 5/2003 |
| WO | WO 03/082406 A2 | 10/2003 |
| WO | WO 03/105921 A2 | 12/2003 |

OTHER PUBLICATIONS

Notice of Reasons for Rejection mailed Mar. 3, 2009 in Japanese Appln. No. 2004-569777, with English translation.

Supplementary European Search Report mailed Jun. 15, 2010 in European Application No. 03793491.6.

* cited by examiner

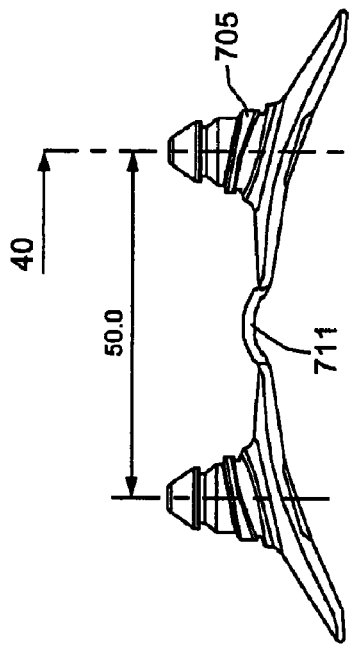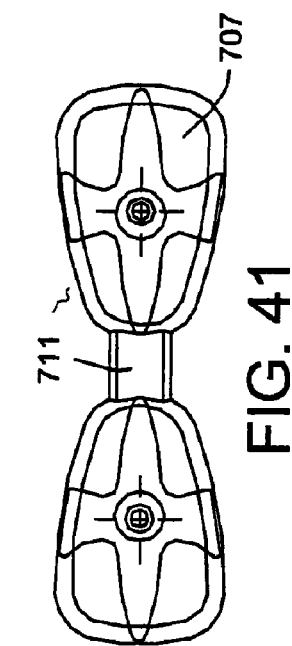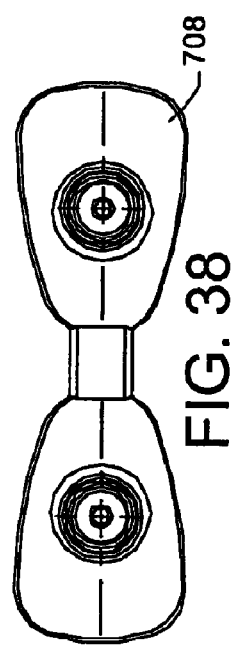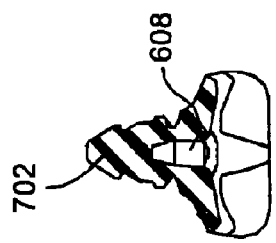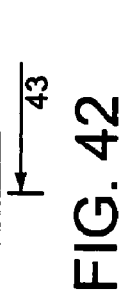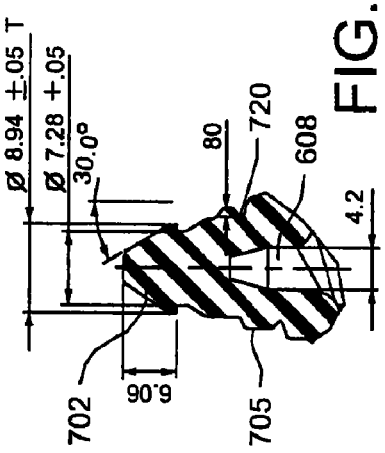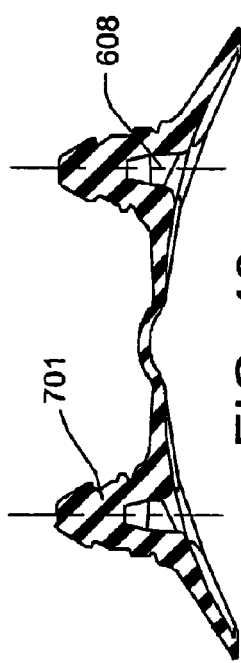

FOREHEAD PAD FOR RESPIRATORY MASK

CROSS-REFERENCE TO RELATED APPLICATIONS

The present application is a continuation of U.S. application Ser. No. 10/655,595, filed Sep. 5, 2003, now U.S. Pat. No. 7,216,647, which claims the benefit of U.S. Provisional Application Ser. No. 60/424,696 filed Nov. 8, 2002 and U.S. Provisional Application Ser. No. 60/467,572 filed May 5, 2003, and which is a Continuation-In-Part of U.S. Non-Provisional application Ser. No. 10/235,846 filed Sep. 6, 2002, now U.S. Pat. No. 6,823,869, which in turn claims priority to U.S. Provisional Patent Application Ser. No. 60/317,486 filed Sep. 7, 2001 and U.S. Provisional Patent Application Ser. No. 60/342,854 filed Dec. 28, 2001. Each of the above applications is hereby incorporated herein by reference in its entirety.

BACKGROUND OF THE INVENTION

1. Field of the Invention

The invention relates to forehead pads. These pads can be used with a respiratory mask for Non-invasive Positive Pressure Ventilation (NPPV) treatment of Sleep Disordered Breathing (SDB).

2. Background of the Invention

Nasal masks are commonly used in the treatment of respiratory conditions and sleep disorders by delivering a flow of breathable gas to a user to either assist the user in respiration or to provide a therapeutic form of gas to the user to prevent sleep disorders such as obstructive sleep apnea (OSA). These nasal masks typically receive a gas through a supply line, which delivers the gas into a chamber formed by walls of the mask.

The mask is generally semi-rigid and has a face portion that is in communication with the nose and/or mouth of a user. The mask is normally secured to the user's head by straps. The straps are adjusted to pull the mask against the face with sufficient force to achieve a gas-tight seal between the mask and the user's face. Gas is thus delivered to the mask through the aperture to the user's nasal passages and/or mouth.

One of the problems that arises with the use of the mask is that in order for the straps to be tight, the mask is compressed against the user's face and may push unduly hard on the user's nose. Additionally the mask may move around on the user's face. Therefore, masks often contain a forehead support that creates addition contact points between the mask and the user's head. The forehead support minimizes the movement of the mask as well as minimizes uncomfortable pressure points of the mask by preventing the mask from pushing too strongly against the user's nose and/or facial region.

Forehead supports typically have attached thereto a soft comfortable patient-contacting forehead pad. Forehead pads are generally constructed from soft materials, such as silicone, in contrast to the forehead support, which is generally rigid. One form of prior art forehead pad is disclosed in U.S. Pat. No. 6,119,693, the contents of which are hereby incorporated by reference in their entirety.

A problem with existing forehead pads is the mechanism by which the pad is connected to forehead support. The pad must be secured in such a way so as to be easy to insert and remove, but not be unintentionally dislodged. Furthermore, regardless of the relative proximity between the forehead support/pad and the mask frame, there should be no sharp edges against which the user's face can make contact, leading to further discomfort.

One form of known forehead pad is used on the AIR PILOT mask, manufactured by MPV, Truma, Germany, shown in FIGS. 50 to 57. This forehead pad includes a stalk adapted to be pulled through a hole on an arm of a forehead support. The pad also includes two rows of three slots adapted to engage with two rows of three teeth which project rearwardly from the arm of the forehead support. Problems with this type of forehead pad include: (i) it is difficult to assemble; (ii) it is difficult to remove; (iii) it may become dislodged during the night and present sharp teeth to the forehead of a patient; (iv) it has a vague assembly which makes it difficult to know when it is in the correct position; (v) its construction leads to regions of high pressure under the teeth; and (vi) it presents an edge to the forehead of a patient when rocked at an angle.

A further problem with existing forehead pads is that they can lead to uneven pressure on the user's forehead, leading to discomfort and marks on the face. For example, one form of known forehead pad includes a patient contacting surface and a pair of reinforcing struts, as shown in FIGS. 16 to 17. During use, the pad is subject to a compressing force that can lead to pressure points, lines or ridges on the patient contacting surface in the region where the reinforcing struts join it. This can lead to uneven pressure on the user's forehead. The use of existing forehead pads also results in sweating by the user.

Another problem with a known form of forehead support is the mechanism for engaging the forehead pad with the forehead support. The forehead support includes a pair of rigid L-shaped catches c adapted to slidably engage with a recess in the forehead pad, as shown in FIGS. 18 to 20. A problem can arise if a pad is not in position when the forehead support is in use: the catch may abut against the forehead of a user. This can lead to discomfort and marking of the forehead.

Therefore, there exists a need in the art for a forehead pad that overcomes the problems listed above.

SUMMARY OF THE INVENTION

One aspect of the invention is directed towards a mask assembly having a forehead support and a forehead pad that provide more comfort to a user.

Another aspect of the invention is directed towards a forehead pad that distributes contact pressure around the user's forehead.

Another aspect of the invention is directed towards a forehead pad that permits a wide range of motion.

Another aspect of the invention is directed towards a forehead pad that lessens or avoids contact between the user and the edges of the forehead pad.

Another aspect of the invention is directed towards a forehead pad that achieves an even pressure distribution with no localized regions of high forces.

Another aspect of the invention is directed towards providing a forehead pad that is easy to insert in a forehead support and is flexible enough to accommodate a range of different forehead sizes and shapes.

Another aspect of the invention is directed towards a forehead pad that tapers smoothly from the support post to the base region, causing lines of force to be smoothly and evenly carried from the support post to the base region, resulting in an even distribution of the pressure across a user's forehead.

Another aspect of the invention is directed towards a forehead pad for a forehead support of a respiratory mask that comprises a plate region connected to a support post, the support post including a forehead support engaging mechanism.

Another aspect of the invention is directed towards a forehead pad that it is relatively easy to engage with a forehead support but relatively more difficult to disengage.

Another aspect of the invention is directed towards a forehead pad that lessens or avoids contact between the user and the edges of the forehead support.

Another aspect of the invention is directed towards a forehead pad that includes a base portion to contact a user's forehead, a support post comprising a necked down region connected to the base portion, and a head adapted to connect the support post to a forehead support of a respiratory mask.

Another aspect of the invention is directed towards a forehead pad assembly that includes at least two pads, each pad comprising a base portion to contact a user's forehead, a support post comprising a necked down region connected to the base portion, and a head adapted to connect the support post to a forehead support of a respiratory mask. The assembly further comprises at least one connector to connect adjacent base portions.

Other aspects, features and advantages of this invention will become apparent from the following detailed description when taken in conjunction with the accompanying drawings, which are a part of this disclosure and which illustrate, by way of example, principles of preferred embodiments.

BRIEF DESCRIPTION OF FIGURES

FIG. 38 is a rear view of another embodiment a forehead pad according to the present invention;

FIG. 39 is a top view of the embodiment shown in FIG. 38;

FIG. 40 is a cross-sectional view of the embodiment shown in FIG. 38 along axis 40-40;

FIG. 41 is a front view of the embodiment shown in FIG. 38;

FIG. 42 is an end view of the embodiment shown in FIG. 39;

FIG. 43 is a cross-sectional view of the embodiment shown in FIG. 42 along axis 43-43;

FIG. 44 is an expanded cross-sectional view of the embodiment shown in FIG. 42;

DETAILED DESCRIPTION OF ILLUSTRATED EMBODIMENTS

Figure 1:
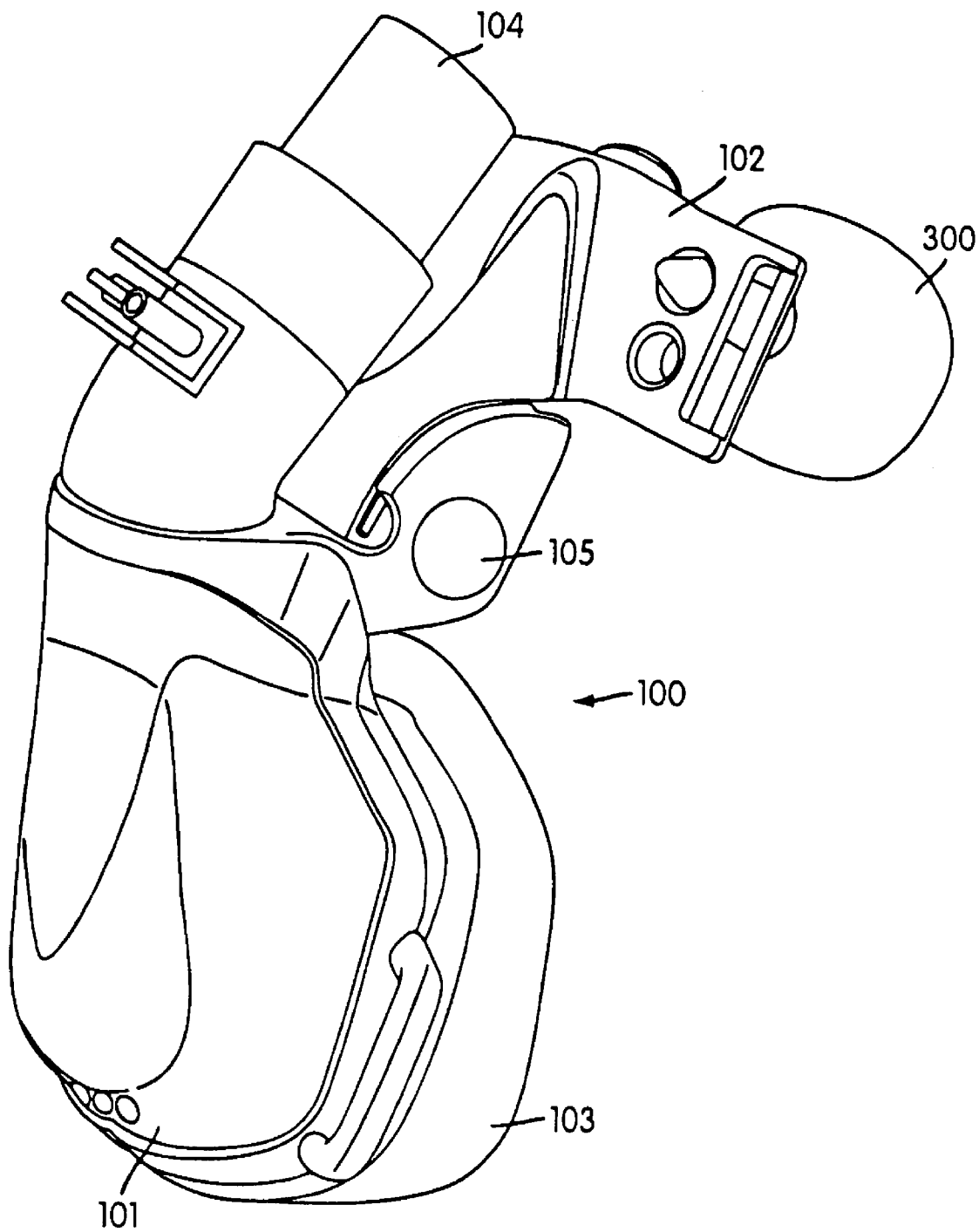
FIG. 1 is a perspective view of a respiratory mask and forehead pad according to one embodiment of the present invention.

FIG. 1 shows an example of a respiratory mask assembly 100. The mask assembly includes a frame portion 101, a forehead support 102, and a forehead pad 300. The mask is adapted to fasten securely and comfortably to a user's face. In particular, the mask assembly 100 comprises a seal-forming region 103 that covers the user's nose and/or mouth and a contains opening 104 to which an air delivery tube can be attached. Air or oxygen flows through the opening 104 under positive pressure.

The forehead support 102 is advantageously connected to the frame portion 101 of the mask assembly 100, e.g., by a pivot device 105, which can be adjusted to allow the forehead support 102 to the accommodate the configuration of a user's face. The forehead support 102 is preferably made from a thermoplastic material. One embodiment of a forehead support is shown in greater detail in FIG. 2.

Figure 2:
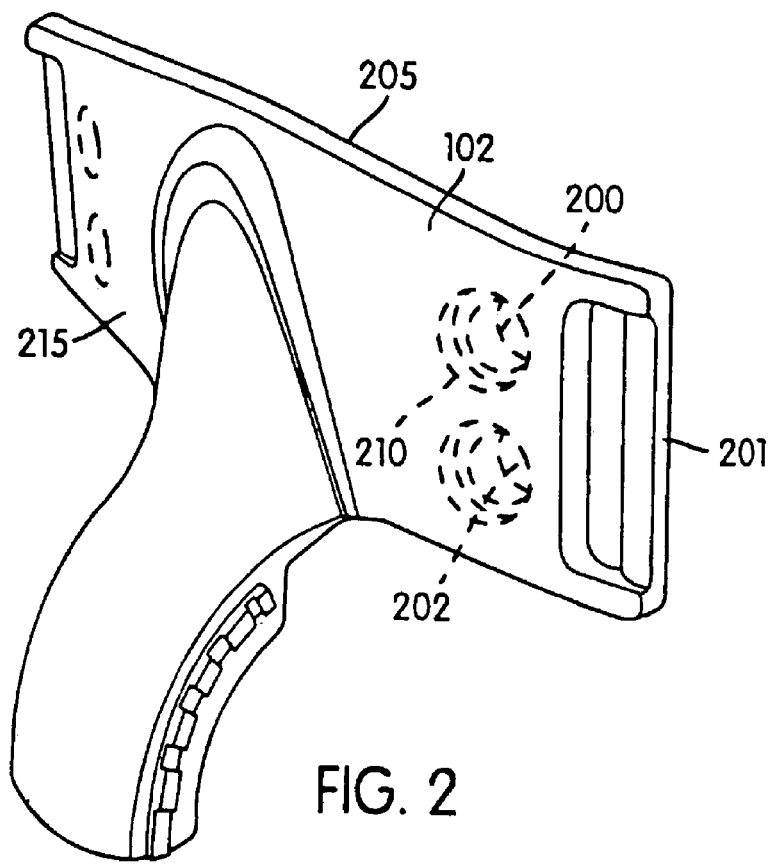
FIG. 2 is a perspective and enlarged view of the forehead support shown in FIG. 1, without the mask frame and pads.

The forehead support 102 can be configured to be essentially straight or it can be curved. The essential straight embodiment is shown in FIG. 2. In the case where the forehead support is curved, the curvature generally follows the curvature of the user's forehead. While this is the most likely structure, it is within the scope of the present invention to use a forehead support 102 that has the opposite curvature, or any combination thereof.

The forehead support 102 can be provided with one or more openings. These openings can be adapted to serve numerous purposes including points of connection to the mask frame, points of connection to any another support surface, points of connection 201 for straps to secure the mask to the user, and apertures 202 for a forehead pad.

In a preferred embodiment of the forehead support 102, the apertures 202 are designed to receive a head of the forehead pad 300. The apertures 202 can be disposed about the forehead support 102 in a manner to allow a user to adjust the position of the forehead pad 300. The apertures 202 are also designed to allow a user to attach the forehead pad 300 securely to the forehead support 102. In a preferred embodiment, the apertures 202 designed to allow a user to attach the forehead pad 300 securely and reversibly to the forehead support 102.

Figure 3:
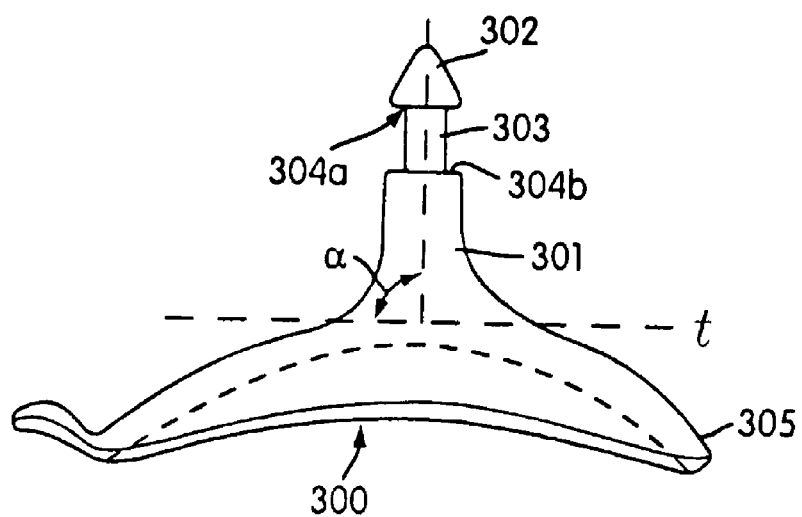
FIG. 3 is a perspective view of one embodiment of a forehead pad according to the present invention.

The forehead pad 300 in accordance with a first embodiment of the invention is shown in greater detail in FIG. 3. The forehead pad 300 comprises a base portion 305 to contact a user's forehead, a support post 301 connected to the base portion, and a head 302 adapted to be connected to the forehead support 102. In this embodiment, the head 302 is bullet or cone shaped, or otherwise tapered. However, other shapes are possible as long as they serve the purpose of the invention.

The base portion 305, support post 301, and head 302 can be separate pieces, designed to fit with each other. In one embodiment, the base portion 305 and the support post 301 can be constructed as one piece. In another embodiment, the support post 301 and the head 302 can be constructed as one piece. In yet another embodiment, the base portion 305 and the head 302 can be constructed without a support post 301. Finally, in a preferred embodiment, the base portion 305, the support post 301, and the head 302 are molded integrally into one piece.

The embodiment shown in FIG. 3 contains a necked down region 303 between the base of the head 302 and the top of the support post 301. In a preferred configuration, the forehead pad is adapted to releasably engage with the forehead support 102. The function of the necked down region 303 is to facilitate this feature. The necked down region 303 is such that its diameter is smaller than the diameter of the base of the head 302. This results in a lip 304a between the base of the head 302 and the necked down region 303 and another lip 304b between the necked down region 303 and the support post 301.

In a preferred embodiment, the necked down region 303 is at least as long as the length of the aperture 202 (FIG. 2) in the forehead support 102. Insertion of the pad 300 through a first end 200 of the aperture in the forehead support 102 results in the head 302 passing through the aperture 202 and emerging out a second end 210. The support post 301 remains on the side of the first end 200 of the aperture 202 with the necked down region 303 occupying at least the length of the aperture. This feature results in easy insertion and a tight fit.

Typically, this insertion can be carried out by a user by applying axial pressure to the base portion 305 of the pad 300. While the support post 301 is flexible, it can withstand the forces needed for assembly. Using the forehead pad embodiment described in FIG. 3 and the forehead support described in FIG. 2 as examples, the head 302, as well as the lip 304a distort as axial force is applied against the first end 200 of the aperture 202, until the head and lip 302 and the lip 304a reach a second end 210 of the aperture 202, whereupon the lip 304a re-expands to engage a first surface 215 of the forehead support 102 adjacent to the aperture 202. Further, the lip 304b abuts against a second surface 205 of the forehead support 102, to prevent axial movement of the pad 300.

The removal of the pad occurs by applying a pulling force it in a direction opposite to the axial force applied for insertion. Once again, the head 302 and the lip 304a distort as the lip 304a disengages with the first surface 215 of the forehead support 102 adjacent to the aperture 202. Lip 304a disengages with the second surface 205 of the forehead support 102. Both the head 302 and the lip 304a regain their original shape after disengagement from the forehead support 200.

The pressure can be applied by a user's fingers and the successful insertion of the pad 300 is indicated not only by the emergence of the head 302 through the first surface 215 of the aperture 202 but typically also by a clicking sound. The combination of sight, sound, and ease of insertion is useful for aged or otherwise infirm users with limited manual and/or digital dexterity. The sound produced has the added benefit of providing the user of knowledge that the pad 300 has been successfully inserted in the dark. This feature can be of importance due to the fact that the masks are used at night. Both the forehead support 102 and the forehead pad 300 are configured such that the pad 300 can be placed in different positions on the support 102 so as to achieve different positions of contact on the user's forehead.

A wide variety of methods well known to a person skilled in the art for the manufacture of the base portion, support post, and head. A preferred method of manufacture is by injection molding.

The support post 301 can project from the base portion 305 at an angle α, defined between a tangent t to the outer surface of the base portion 305 at a point of contact between the support post 301 and the base portion 305. This angle α can be about 90°, i.e., the support post 301 extends essentially straight out from the base portion 305. FIG. 3 shows an embodiment of a forehead pad 300 in which the angle α is about 90°.

Figure 4:
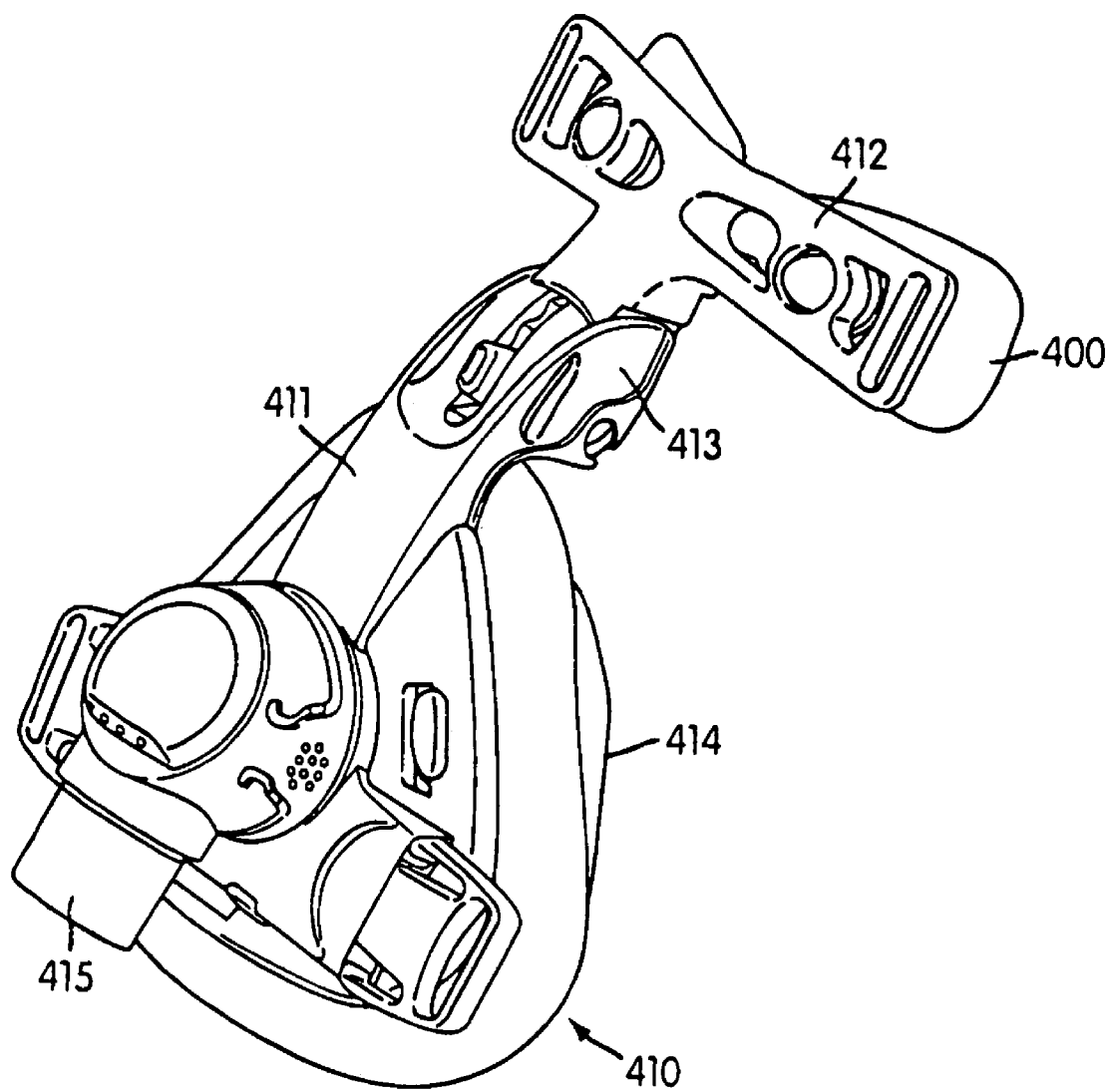
FIG. 4 is a perspective view of a respiratory mask and forehead pad according to one second embodiment of the present invention.

FIG. 4 shows another embodiment of a respiratory mask assembly 410. The mask assembly 410 includes of a frame portion 411, a forehead support 412, and another embodiment of a forehead pad 400. The forehead support 412 is advantageously connected to the frame portion 411 of the mask 410, e.g., by a pivot device 413. The mask assembly 410 comprises a seal-forming cushion 414 that covers a user's nose and/or mouth and contains a swivel elbow 415. The swivel elbow 415 is adapted to receive a supply of air or oxygen flows at positive pressure.

Figure 5:
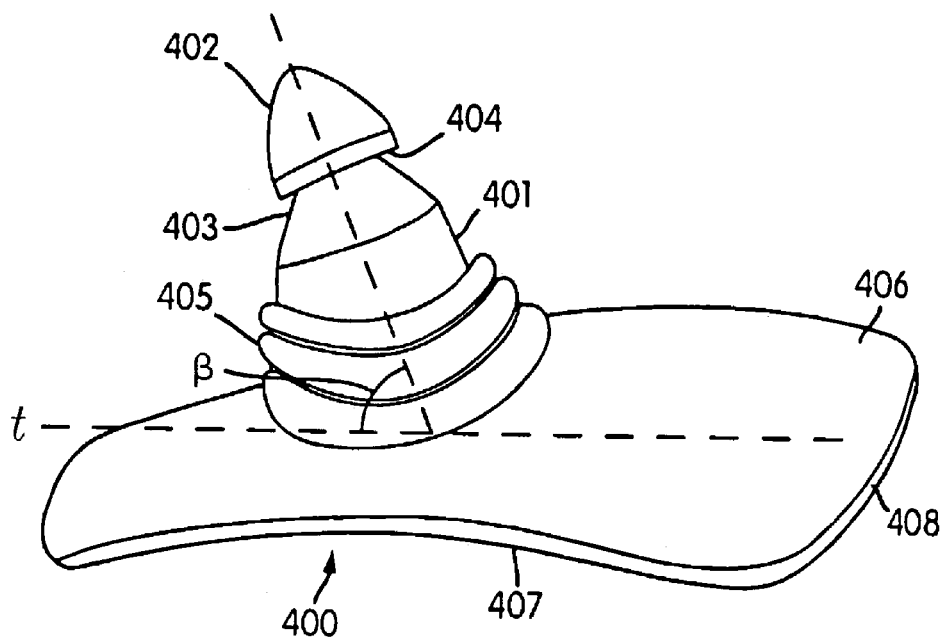
FIG. 5 is a perspective view of another embodiment of a forehead pad according to the present invention.
Figure 6:
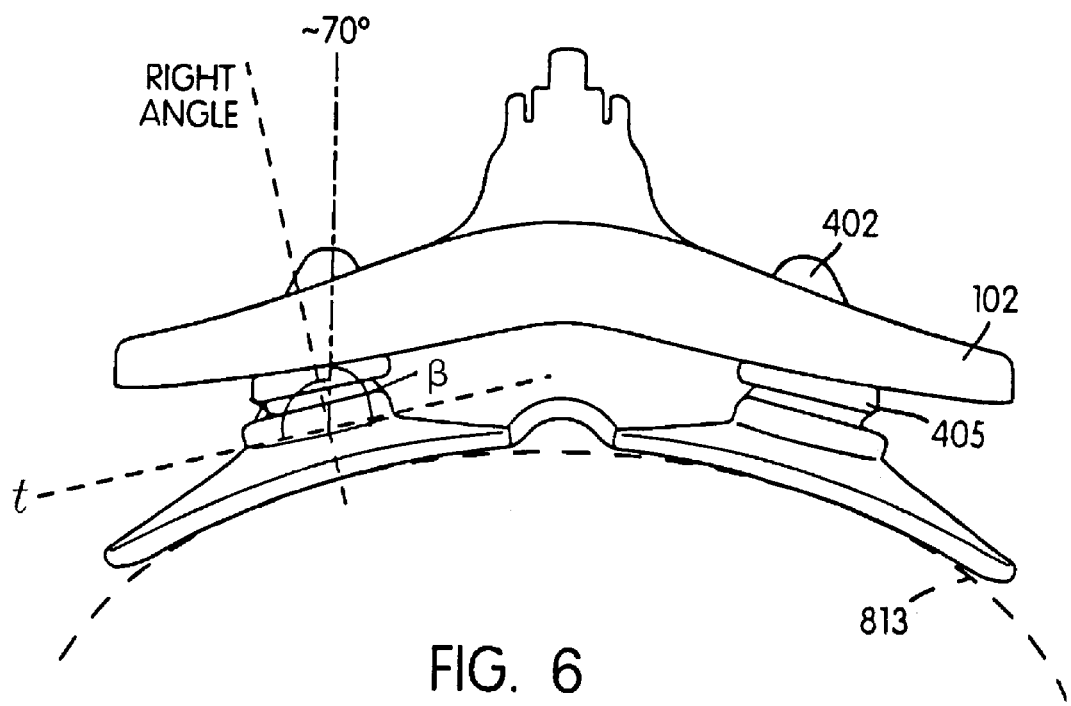
FIG. 6 is a top view of a forehead support including a pair of forehead pads and a forehead of a user.

FIG. 5 shows another embodiment of a forehead pad 400 in greater detail. This embodiment of the pad 400 includes a base portion 408, a support post 401, and a head 402. The general construction and operation is similar to that of the first embodiment although there are several differences in the construction, for example, the angle β between the tangent t to the outer surface of the base portion 406 at a point of contact between the support post 401 and the base portion 408 is between about 60° and about 120°. Preferably, the angle β is about 70°. One advantage of a support post 401 projecting at an angle less than 90° is to allow the base portion 400 to better fit the contours of a user's forehead, as shown in FIG. 6.

The support post 401 can be constructed in a manner so as to make it more flexible. For example, the support post 401 includes cut away portions 405. These cut away portions help the support post to be able to be bent or flexed, varying the angle β in use. In this way, a support post 401 of larger diameter may be used while still retaining a degree of flexibility as shown in FIGS. 68 to 71.

Figure 58:
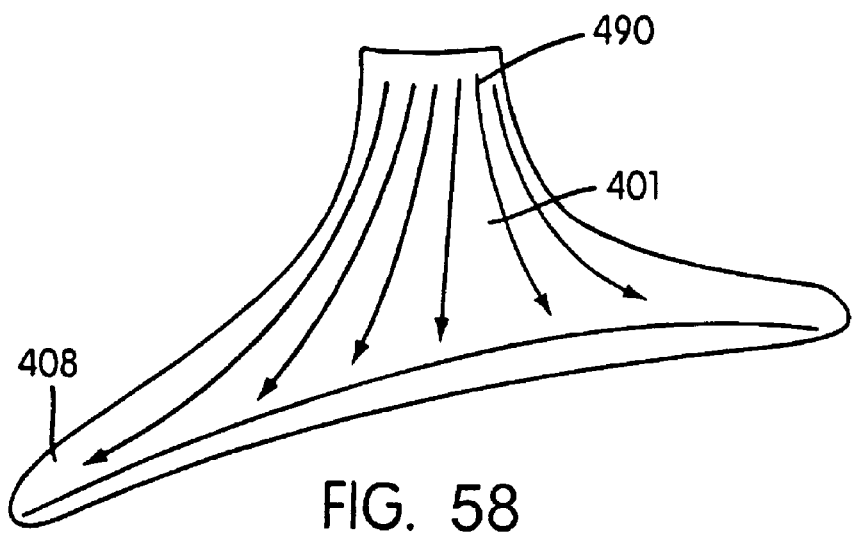
FIG. 58 is a top view of another embodiment of a forehead pad according to the present invention.
Figure 59:
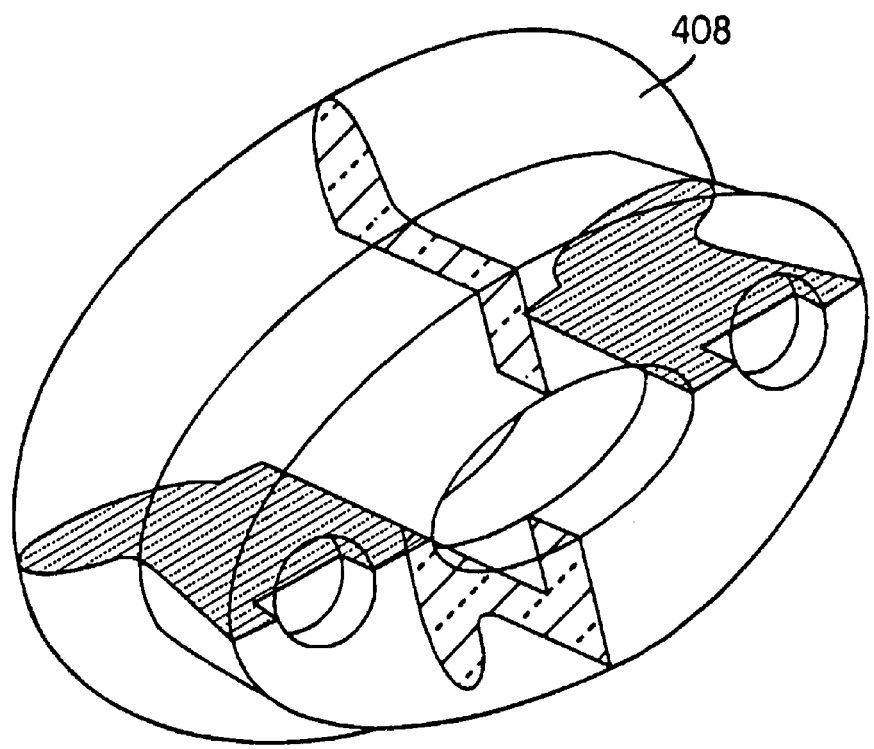
FIG. 59 is a front perspective view of another embodiment of a forehead pad according to the present invention.
Figure 60:
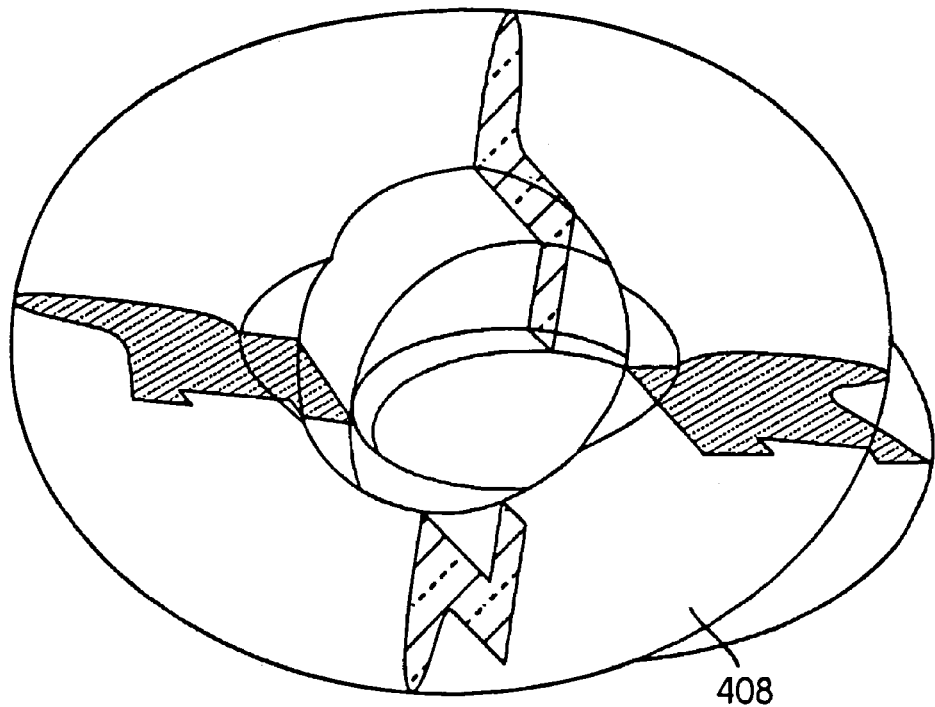
FIG. 60 is a rear perspective view of the forehead pad shown in FIG. 59.
Figure 61:
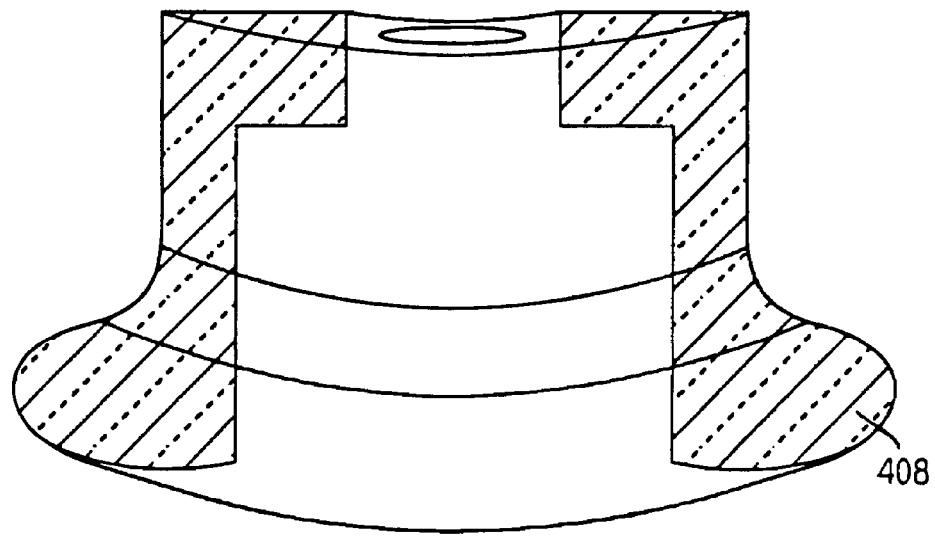
FIG. 61 is a cross-sectional view of the forehead pad shown in FIG. 59 along the minor axis.
Figure 62:
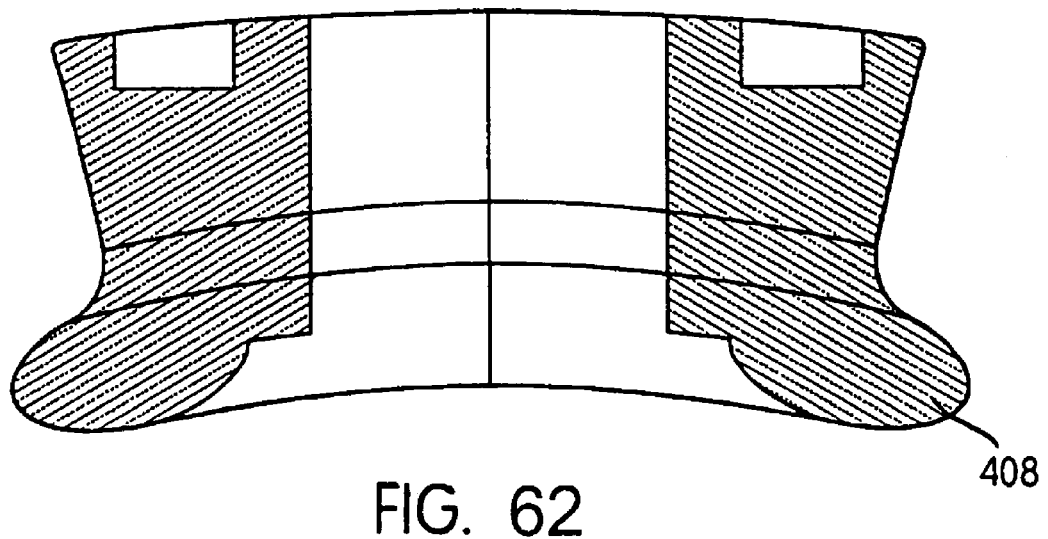
FIG. 62 is a cross-sectional view of the forehead pad shown in FIG. 59 along the major axis.

The base portion 408 can be of any shape, preferably in a pad-like configuration. In one embodiment, a contact region 407 of the base portion 408 is shaped so that the transmission of contact forces to the surface of the forehead of the user takes place under physiologically compatible pressures, as shown in FIG. 58. In a preferred embodiment, the contact region 407 is concavely curved to follow the curvature of a forehead.

Figure 7:
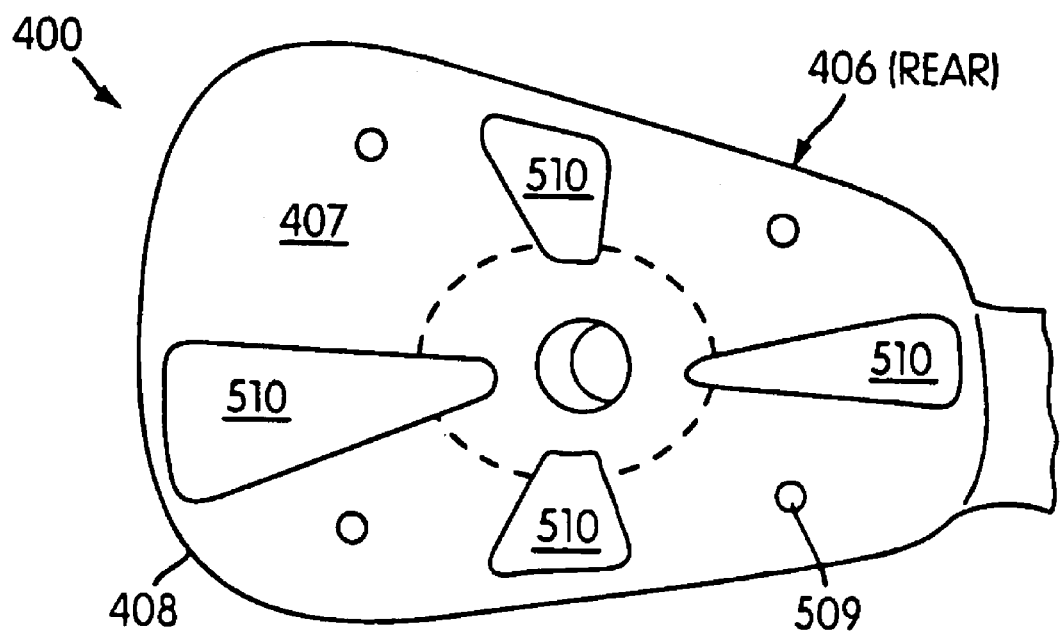
FIG. 7 is a perspective view of the contact surface of one embodiment of a forehead pad showing raised surfaces.

The contact region 407 can optionally include a raised surface pattern 510 as shown in FIG. 7. The pattern 510 reduces the possibility of a suction effect of the pad 400 thereby reducing the drawing of blood in the region and making the pad 400 more comfortable. The raised pattern 510 has the added benefit of reducing sweating. In another embodiment, a rear surface of the pad 400 is given a sand-blasted finish to improve ventilation and reduce the likelihood of sweating.

Figure 8:
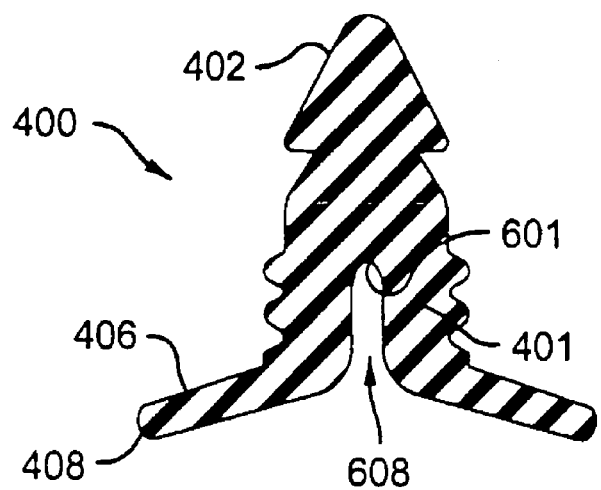
FIG. 8 is a cross-sectional view of one embodiment of a forehead pad showing a hollowed out region.

The base portion 408 and support post 401 of the pad 400 can also include a hollowed out region 608 extending a predetermined distance 601 into the base portion 408 and/or the support post 401 as shown in the cross-sectional view in FIG. 8. In the embodiment shown, the hollowed out region 608 extends through the base portion 408 and partly into the support post 401. This structure imparts a degree of springiness and flexibility to the forehead pad 400. Due to the essentially incompressible nature of silicone, some cut-away regions 405 assist flexibility. The use of the hollowed out region 608 allows for some movement along an axis through the support post 401.

Increasing the diameter of the support post 401 makes the forehead pad 400 easier to insert into the forehead support 102. Furthermore, a larger diameter reduces the likelihood of localized pressure points. However, as the support post 401 is made thicker, it becomes less flexible. Hence the preferred embodiment of the invention balances ease of insertion with flexibility.

In another embodiment, the hollowed out region 608 extends through the base portion 408, the support post 401, and the head 402 resulting in a through-bore 509 (shown in FIG. 7). The through-bore 509 may further facilitate compression of the support post 401 and head 402 during assembly and disassembly. This structure allows a flow of air and/or moisture to occur from the user's skin to the atmosphere, resulting in a reduction of sweating and a more comfortable pad 400.

Figure 9:
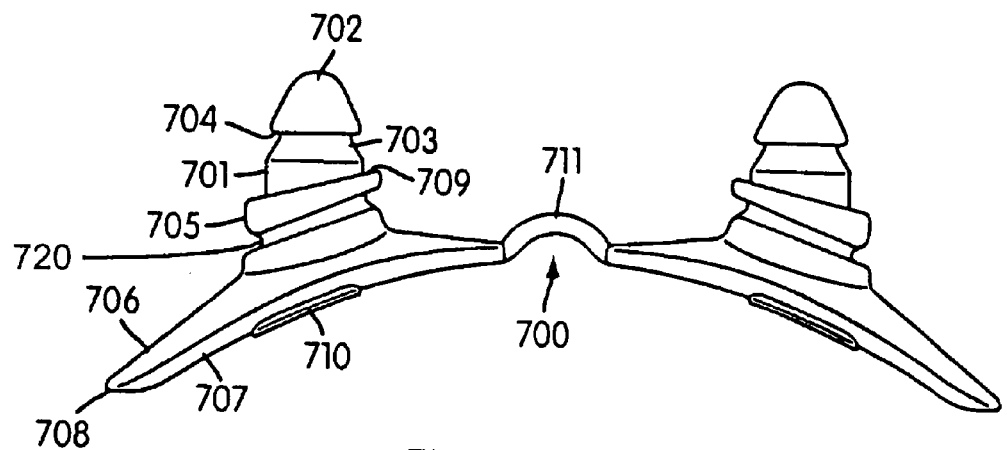
FIG. 9 is a top view of an embodiment of a forehead pad assembly showing two pads joined by a flexible connector.

The support post 401 has a diameter that is in its broadest aspect between about 0.1 cm and about 3.0 cm. More specifically the diameter of the support post of the embodiment of FIG. 9 is between about 0.5 cm and about 1.25 cm, and most preferably the diameter is about 1 cm. The term "about" is meant to indicate that the diameters are not absolute and can be deviated by one skilled in the art. Alternative embodiments, such as those shown in FIGS. 21 to 31 have different diameters.

Figure 37:
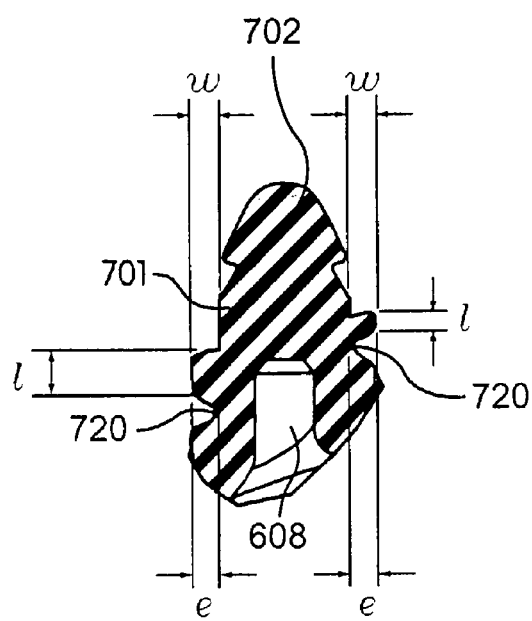
FIG. 37 is a an expanded cross-sectional view of the embodiment shown in FIG. 35.

The support post 401 has a length that is in its broadest aspect between about 0.1 cm and about 2.5 cm. More specifically the length is between about 0.5 cm and about 1.25 cm, and most preferably the length is about 1 cm. Dimensions for one form of forehead pad are shown in FIG. 37. Once again, the term "about" is meant to indicate that the lengths are not absolute and can be deviated by one skilled in the art.

The support post 401 can be straight or it can taper. An example of a straight support post is shown in the embodiment in FIG. 3. The taper can also be such that the region at the base portion is thicker than the head region, as shown in the embodiment in FIG. 5.

As would be understood by one skilled in the art, a wide variety of materials can be used to manufacture the forehead pad in accordance with the present invention. Features of any material used should include biocompatibility, flexibility and comfort. Some examples of such materials include rubber and flexible plastics. In a preferred embodiment, the pad is constructed from cured Liquid Silicone Rubber (Part#2666031, Silastic 94-595-HC) manufactured by Dow Corning, alternatively a silicone with a hardness of approximately 35-45 Shore A may be used. These examples are merely intended to be illustrative and are not limiting in any manner.

In accordance with a preferred embodiment of the present invention, at least two base pads can be joined in a forehead pad assembly 700. In this embodiment, two versions of which are shown in FIGS. 9 and 32 to 44, a connector 711 is used to connect adjacent base portions 708. Any type of connector can be used such as a strap or a flexible bridge portion. An advantage of a connector is that the assembly 700 has a one-piece design which is less likely to be lost. The plurality of base portions 708, with contact regions 707, and connectors 711 can be integrally formed with each other.

As mentioned earlier, the hollowed out region 608 can extend a pre-determined distance into the base portion 708 and/or the support post 701. This distance can be adjusted to increase flexibility of the forehead pad assembly 700. For example, the hollowed out region 608 extends a longer distance into the support post 701 in the embodiment shown in FIG. 44 when compared to the embodiment shown in FIG. 37. Increasing the distance of the hollowed out region 608 has several advantages including flexibility, minimization of contact with the edges of the base portion 708, and better airflow resulting in a reduction in sweating by the user.

The hollowed out region 608 can also have a variety of shapes including conical, pyramidal, cylindrical, or combinations thereof. It is within the scope of this invention that the hollowed out region 608 have additional sub-structures within it including ridges, bumps, or holes.

Figure 10:
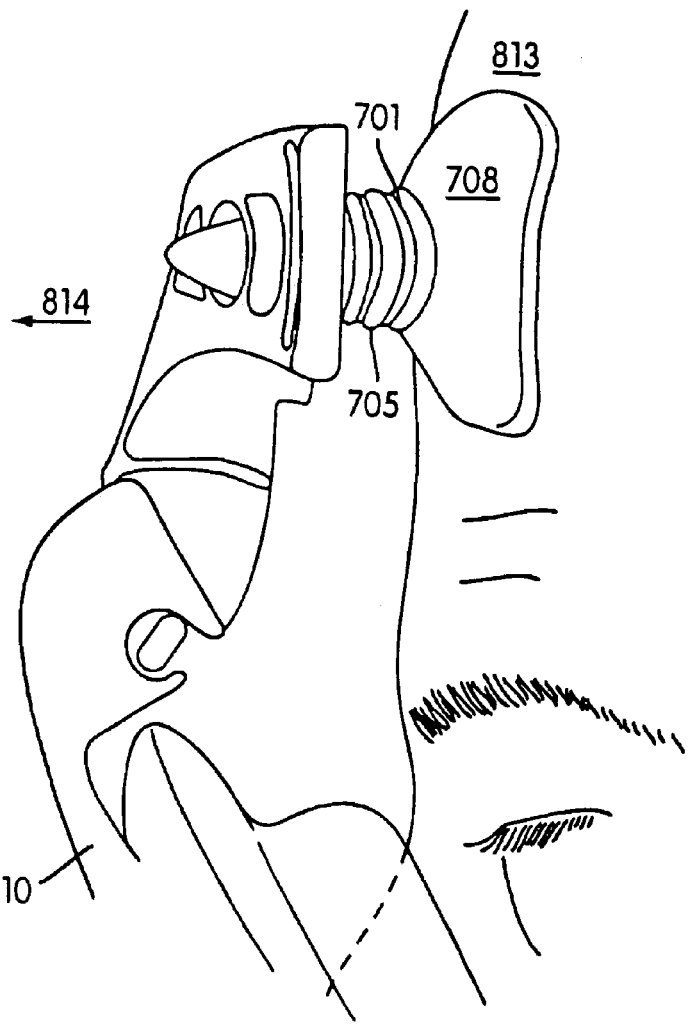
FIG. 10 is a right side view of one embodiment of a forehead pad in a respiratory mask showing contact with a user.

In a preferred embodiment, the two base portions 708 of a forehead pad assembly 700 are adapted in order to be situated above left and right eyebrows of the user. As shown in FIG. 10, a base portion 708 is shown against the user's forehead 813. The support post 701 is designed to act as a spring along the direction of arrow 814. The cut away portions 705 improve its flexibility while maintaining ease of insertion. Another advantage of this design is that it can better accommodate rolling and twisting of the mask 410. A further advantage of the support post 701 is that its diameter is optimized to reduce the effect of a single point of pressure on the forehead 813.

The cut away portions 705 define an undercut 720 between the cut away portions 705 and the base portion 708. The undercut 720 can be a variety of shapes including curved, square, conical, triangular, or any combinations thereof. The undercut 720 depth e can also be varied. The depth e can range between about 0.25 mm to about 1.25 mm, preferably between about 0.5 mm and about 1 mm, and most preferably about 0.75 mm. The term "about" is meant to indicate that the widths and lengths are not absolute and can be deviated by one skilled in the art.

The number, shape, and size, width w, and length l of the cut away portions 705 can be varied to serve a variety of purposes including ease of insertion, ease of removal, flexibility of motion when unassembled with the forehead support, flexibility of motion when assembled with the forehead support, minimization of contact between the user and the edges of the base portion 708, minimization of contact between the user and the edges of the forehead support 102, and angles between the forehead pad assembly 700 and the forehead support 102. The width w can range between about 0.25 mm to about 1.25 mm, preferably between about 0.5 mm and about 1 mm, and most preferably about 0.75 mm. The length l can range between about 0.05 mm to about 1.5 mm, preferably between about 0.25 mm and about 1 mm. Once again, the term "about" is meant to indicate that the widths and lengths are not absolute and can be deviated by one skilled in the art.

The cut away portions 705 can have regions of similar or different widths w and similar or different lengths l. Comparison of the embodiment of the forehead pad assembly 700 shown in FIGS. 32 to 37 with the embodiment of the forehead pad assembly 700 shown in FIGS. 38 to 44 shows a few variations in the cut away portions 705. The width w of the cut away portions 705 in the embodiment shown in FIGS. 38 to 44 is less than the width w of the cut away portions 705 in the embodiment shown in FIGS. 32 to 37.

The undercut 720 in FIG. 40 (a cross-sectional view along line 40-40 of FIG. 39) may be more pronounced than the embodiment of FIGS. 32 to 37. Thus the range of movement of the pad in the vertical plane can be increased, thereby increasing the range of users the mask will fit. In addition, the increased range of movement can help prevent the edge of the pad from coming in contact with the user's forehead, thereby increasing user compliance and comfort. Finally, the increased undercut 720, along with the shape and size of the surrounding cut away portions 705, can effect the force necessary to flex the base portion 708 with respect to the support post 701, thereby optimizing the desired flexing forces within levels acceptable to the user while still allowing adequate performance of the forehead pad assembly 700.

Figure 45:
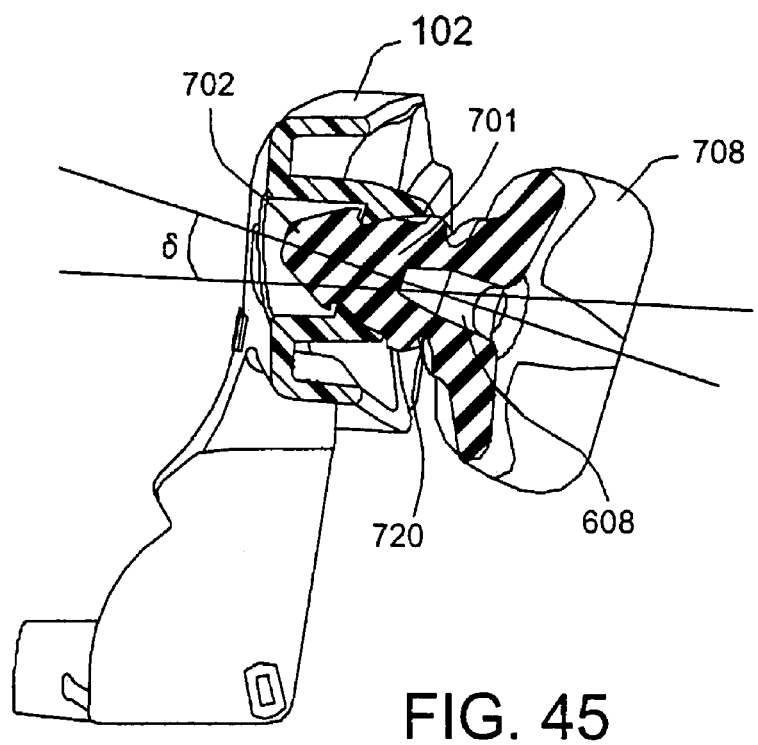
FIG. 45 is a cross-sectional view of one embodiment of a forehead pad engaged with one embodiment of a forehead support according to the present invention.
Figure 46:
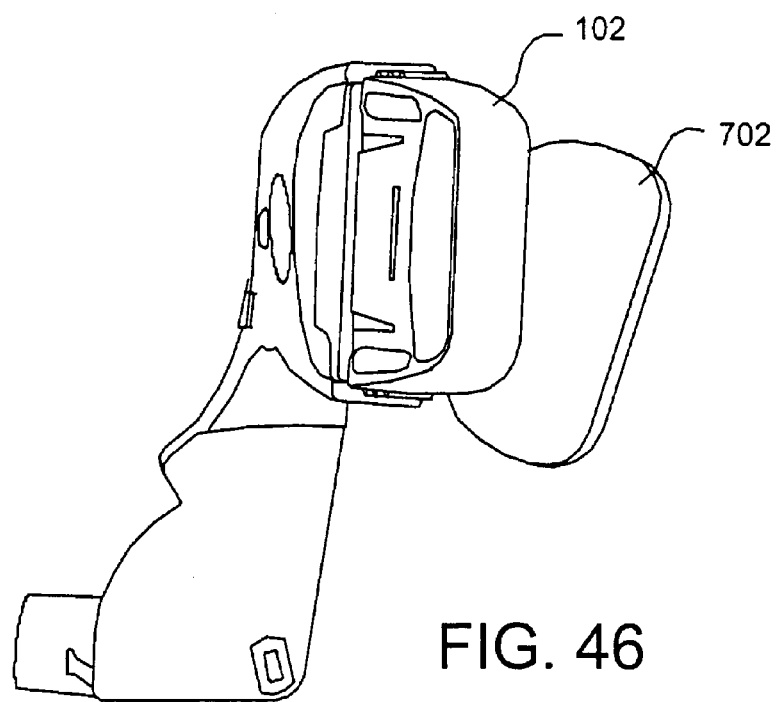
FIG. 46 is side view of the embodiment shown in FIG. 45.

One advantage of reducing the width w and/or increasing the depth e is to vary the angle $\delta$ between the forehead pad assembly 700 and the forehead support 102, which in turn allows for greater range of motion and user comfort. The angle $\delta$ is the angle between a horizontal line h and a line passing through the center of the base portion 708 and the support post 701. FIGS. 45 and 46 show the embodiment of the forehead pad assembly 700 shown in FIGS. 38 to 44 assembled with the forehead support 102. The angle $\delta$ is about 25°. The angle $\delta$ of the embodiment of the forehead pad assembly 700 shown in FIGS. 32 to 37 assembled with the forehead support 102 is about 0°. Once again, the term "about" is meant to indicate that the angles are not absolute and can be deviated by one skilled in the art.

Presentation of the base portion 708 of the forehead pad assembly 700 at an angle which is generally parallel to the users forehead provides improved comfort to the user, reducing the likelihood of pressure sores which may result from an uneven presentation. In some forms of long masks, for example a full face mask, the forehead support 102 may be positioned in use higher up the forehead of the user than in a nasal mask.

In the embodiment of forehead support shown in FIG. 42, the support post 701 and base portion 708 are generally perpendicular to one another when viewed from an end. However, in other embodiments, they may be constructed at different angles. For a long mask, because of the curvature of the skull, in order that the base portion 708 of the forehead pad assembly 700 be presented generally parallel to the user's forehead, either (i) the forehead support 102 should be adapted to retain a perpendicular forehead pad assembly 700 at an angle, as shown in FIG. 45, or (ii) the forehead support 102 should be adapted to retain a non-perpendicular forehead pad assembly 700 at a right angle. In the preferred embodiment, a perpendicular pad is used and the forehead support 102 is adapted to retain and present the pad to the forehead of the user at the appropriate angle. In this way, the same forehead pad assembly 700 can be used across a range of mask systems, for example, nasal masks and full face masks, providing an economic benefit to the manufacturer through the use of common parts.

Figure 11:
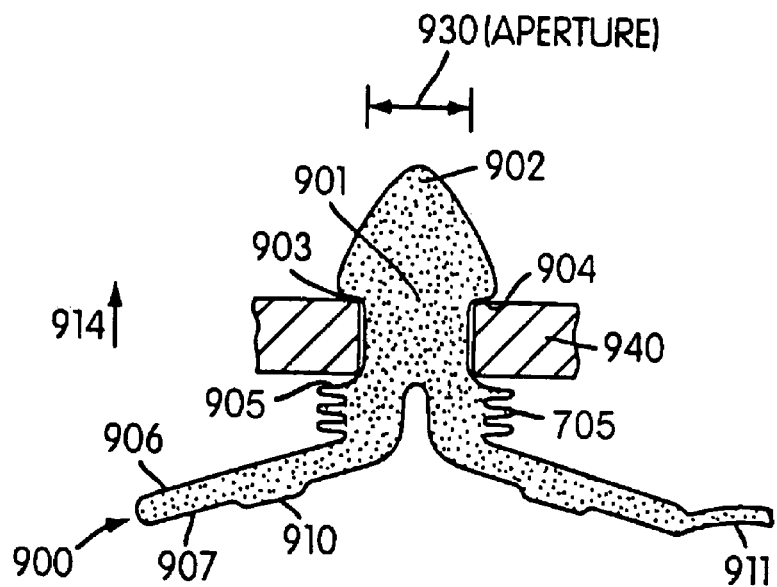
FIG. 11 is a cross-sectional view of one embodiment of a forehead pad engaged with one embodiment of a forehead support.

FIG. 11 shows a cross section of an embodiment of a forehead pad 900 inserted into an aperture 930 in a forehead support 940. To insert the pad 900, axial force is applied in the direction of arrow 914. The head 902 and the lip 904 distort as they pass through the aperture 930. Once the head 902 and the lip 904 are through the aperture 930, the necked down region 903 of the support post 901 occupies the length of the aperture 930. This results in the lip 905 also making contact with the forehead support 940. The engagement of lips 904 and 905 with respective side surfaces of the forehead support 940 results in maintaining the pad 900 in position.

To remove the pad 900 from the forehead support 940 the pad 900 is pulled in an opposite direction to arrow 914. Once again, the head 902 and/or the lip 904 distort as they pass through the aperture 930 enable the pad 900 to disengage from the forehead support 940.

Figure 12:
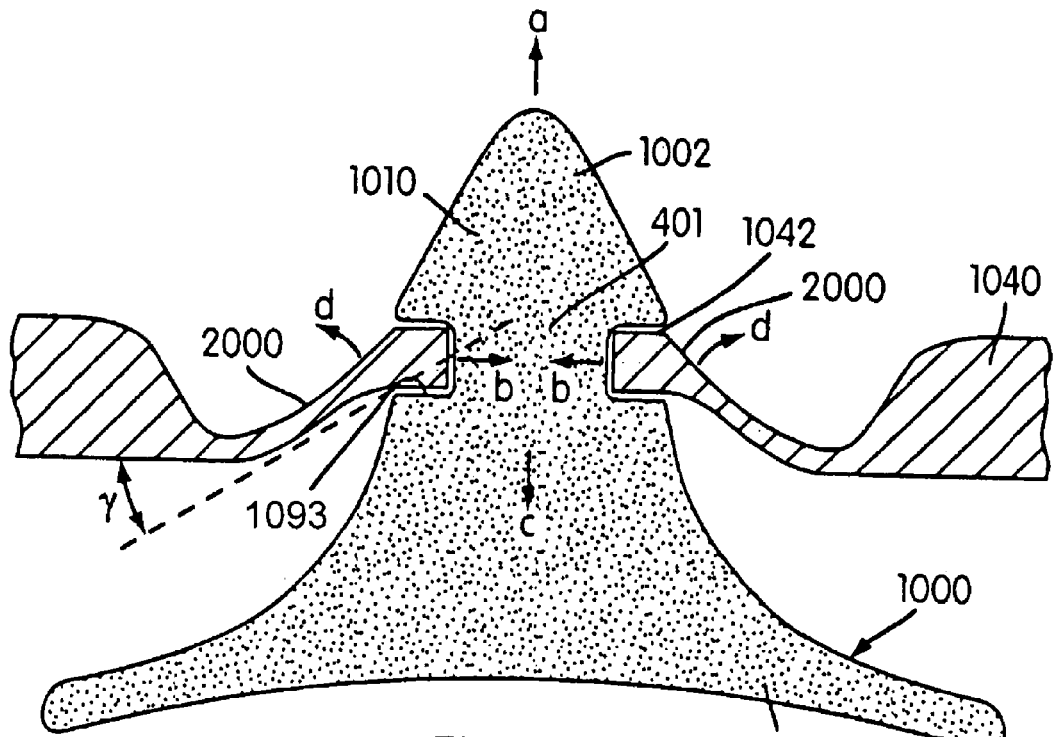
FIG. 12 is a cross-sectional view of another embodiment of a forehead pad engaged with another embodiment of a forehead support.

FIG. 12 shows a cross section of an embodiment of a forehead pad 1000 inserted into another embodiment of a forehead support 1040. The forehead support 1040 has arms 2000 that can move in direction d when pressure is applied to the pad 408 in direction a. In one embodiment, the movement of arms 2000 results in a plastic deformation, i.e., the removal of the pad 408 results in the arms 2000 remaining essentially in the position they were when the pad 408 was inserted. In another embodiment, the movement of arms 2000 results in an elastic deformation, i.e., the removal of the pad 408 results in the arms 2000 returning essentially to the position they were before the pad 408 was inserted. The support post 401 can compress in direction b allowing for ease in insertion and removal but still providing a firm fit. Once inserted, the pad 408 can be adjusted by angle γ.

Figure 13:
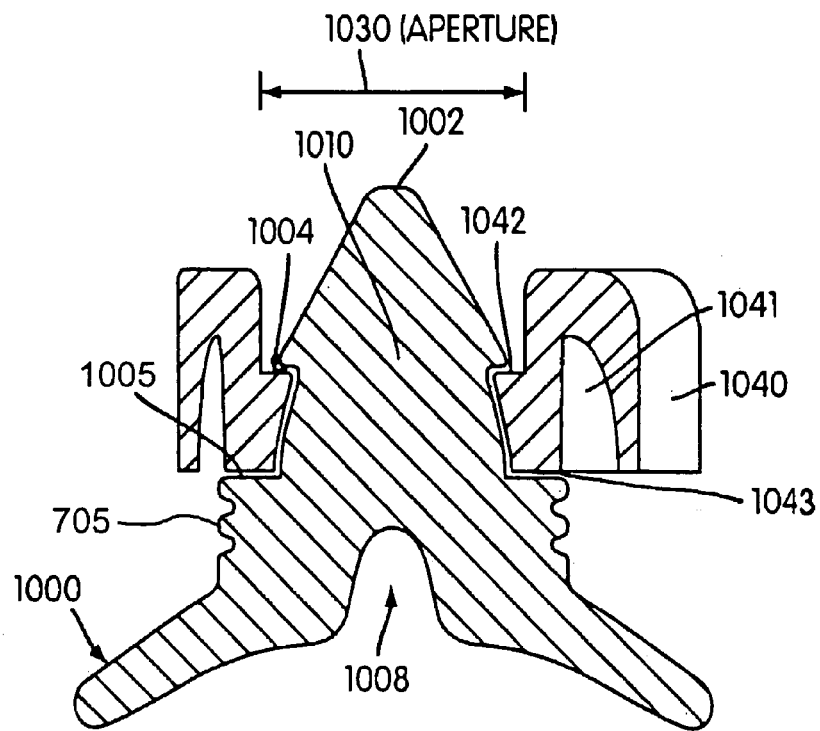
FIG. 13 is a cross-sectional view of another embodiment of a forehead pad engaged with another embodiment of a forehead support.

A cross section of another embodiment of a forehead pad 1000 engaged with a rigid forehead support 1040 is shown in FIG. 13. The forehead support 1040 comprises lips 1042 and 1043. Lip 1042 of the forehead support 1040 is adapted to engage lip 1004 of the head 1002 and lip 1043 of the forehead support 1040 is adapted to engage lip 1005 of the support post 1010. In another embodiment of the invention, the support post 1010 is co-molded to the forehead support 1040.

Figure 14:
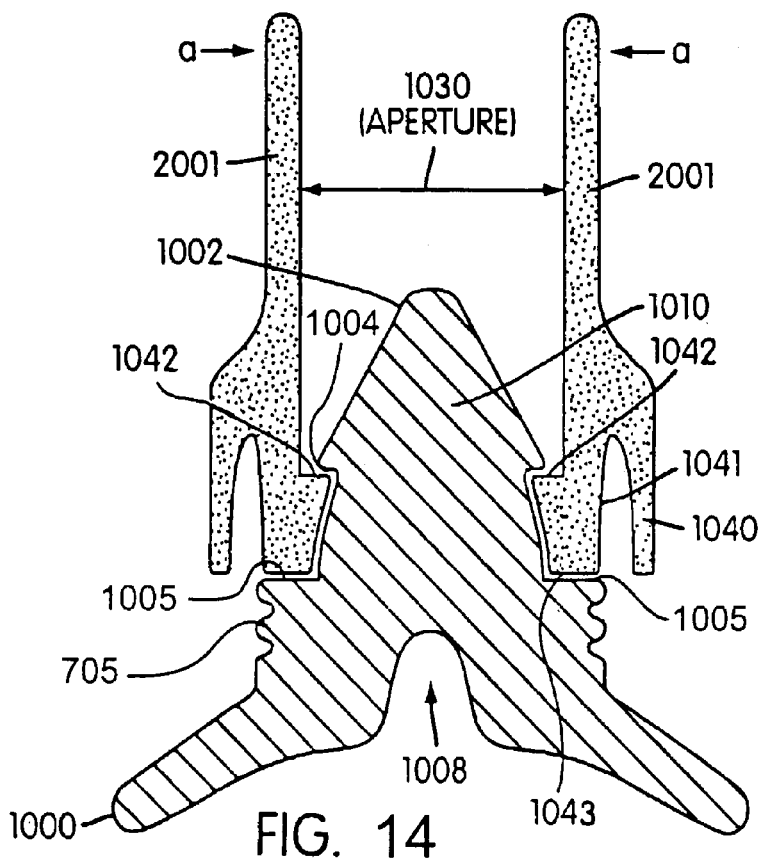
FIG. 14 is a cross-sectional view of another embodiment of a forehead pad engaged with another embodiment of a forehead support.
Figure 15:
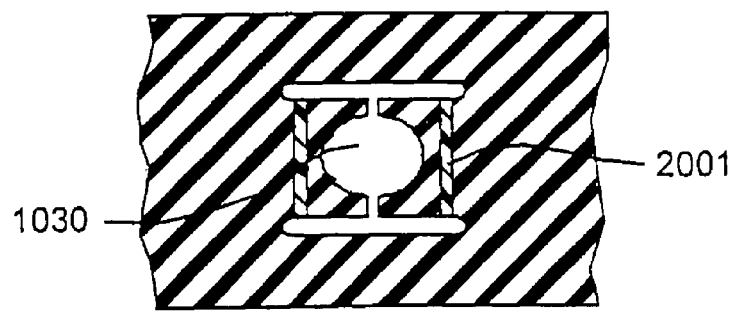
FIG. 15 is a top view of the embodiment of the forehead support shown in FIG. 14.
Figure 16:
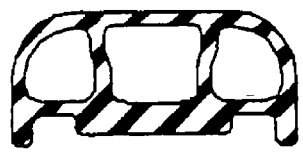
FIG. 16 is a cross-section of a prior art forehead pad.
Figure 17:
FIG. 17 is a cross-section of the forehead pad shown in FIG. 16 in a compressed state.
Figure 18:
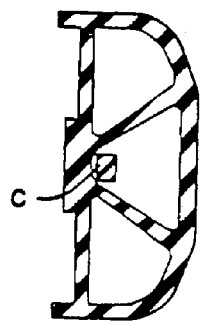
FIG. 18 is a cross-section of a prior art forehead pad.
Figure 19:
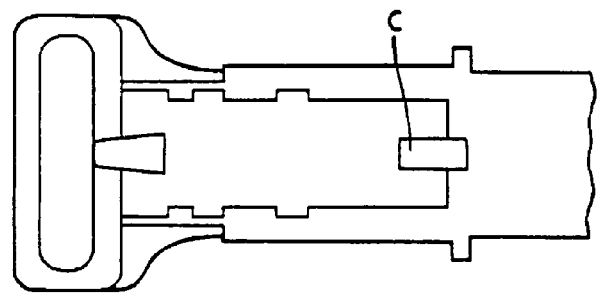
FIG. 19 is a front view of a prior art forehead support.
Figure 20:
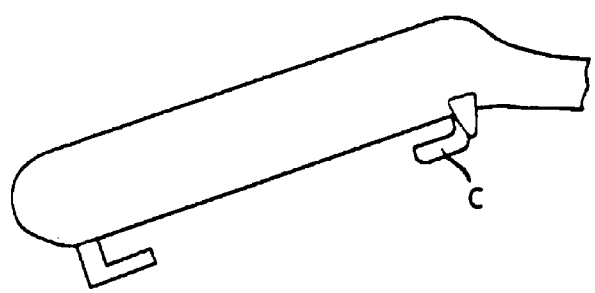
FIG. 20 is a top view of the forehead support shown in FIG. 19.
Figure 21:
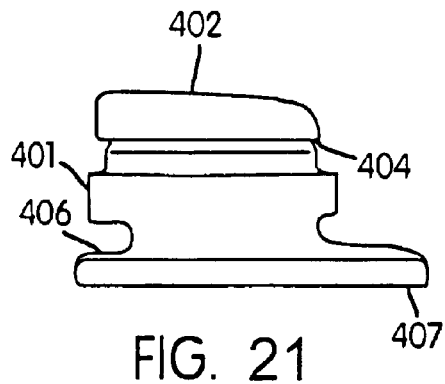
FIG. 21 is a side view of another embodiment of a forehead pad according to the present invention.
Figure 22:
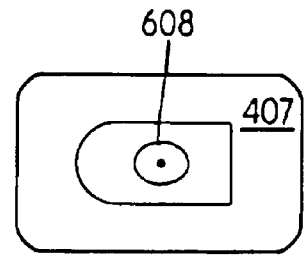
FIG. 22 is a bottom view of the embodiment shown in FIG. 21.
Figure 23:
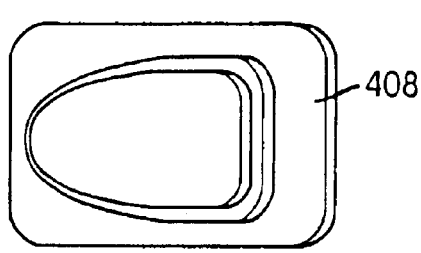
FIG. 23 is a top view of the embodiment shown in FIG. 21.
Figure 24:
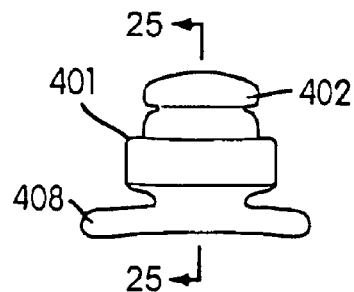
FIG. 24 is another side view of the embodiment shown in FIG. 21.
Figure 25:
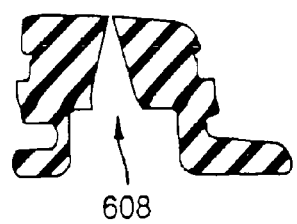
FIG. 25 is a cross-sectional view of the embodiment shown in FIG. 24 along axis 25-25.
Figure 26:
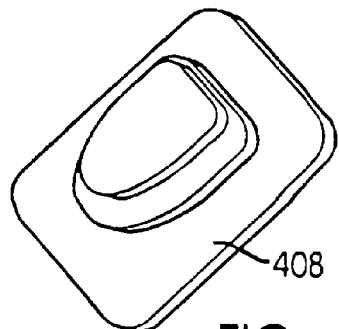
FIG. 26 is a perspective view of the embodiment shown in FIG. 21.
Figure 27:
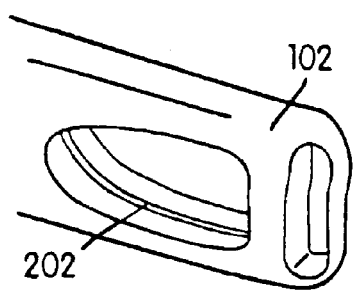
FIG. 27 is a perspective view of another embodiment of a forehead support according to the present invention.
Figure 28:
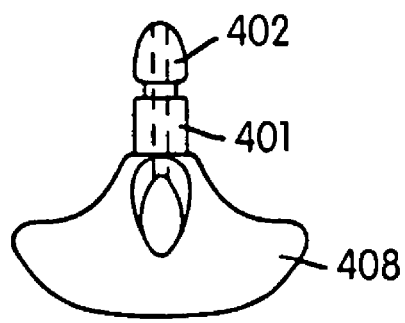
FIG. 28 is an end view of another embodiment of a forehead pad according to the present invention.
Figure 29:
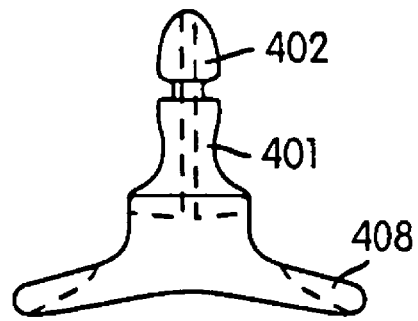
FIG. 29 is a side view of the embodiment shown in FIG. 28.
Figure 30:
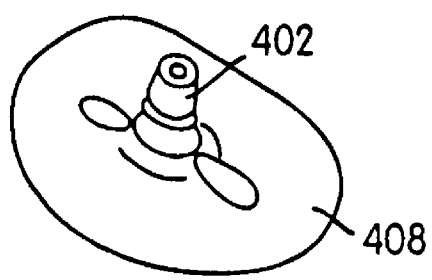
FIG. 30 is a perspective view of the embodiment shown in FIG. 28.
Figure 31:
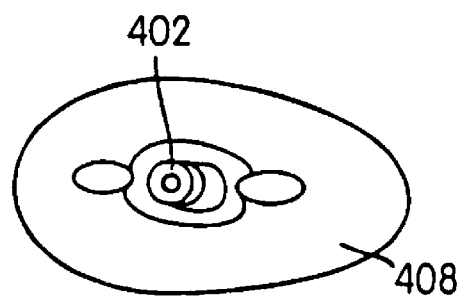
FIG. 31 is a top view of the embodiment shown in FIG. 28.
Figure 32:
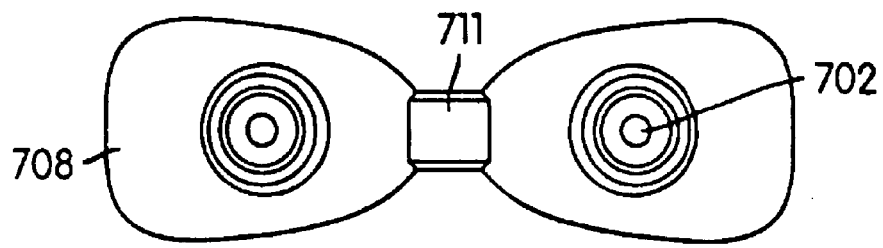
FIG. 32 is a rear view of the embodiment shown in FIG. 9.
Figure 33:
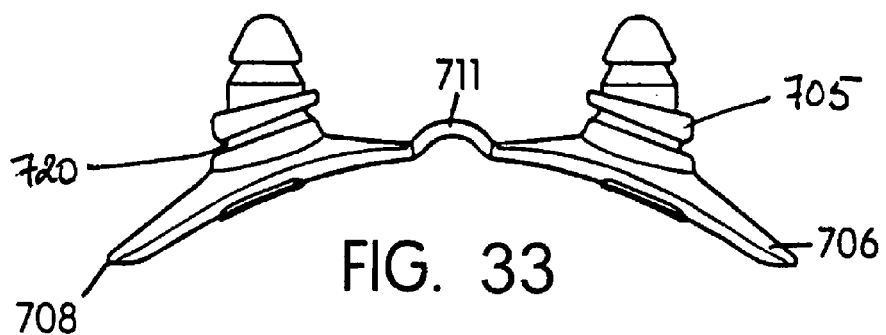
FIG. 33 is a top view of the embodiment shown in FIG. 32.
Figure 34:
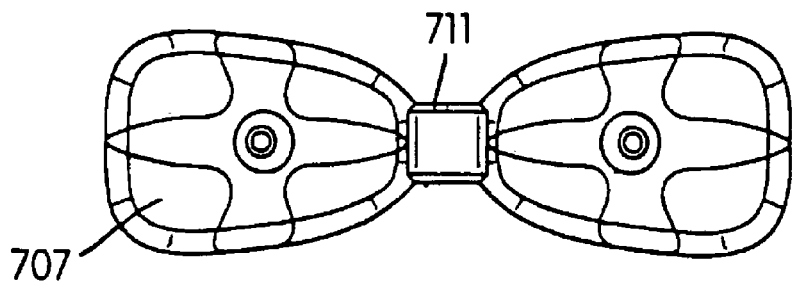
FIG. 34 is a front view of the embodiment shown in FIG. 32.
Figure 35:
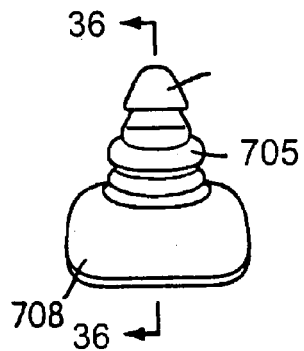
FIG. 35 is an end view of the embodiment shown in FIG. 9.
Figure 36:
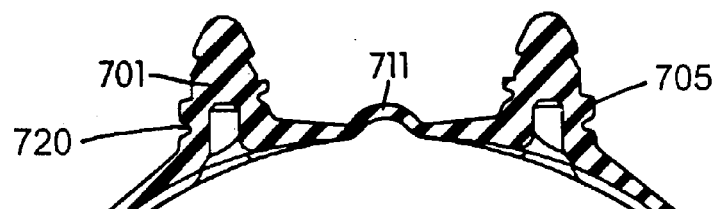
FIG. 36 is a cross-sectional view of the embodiment shown in FIG. 35 along axis 36-36.

FIGS. 14 and 15 shown another embodiment of a forehead pad 1000 engaged with an embodiment of a forehead support 1040. The forehead support 1040 has arms 2001. These arms 2001 define the aperture 1030 and can be moved in direction a to allow for removal of the pad 1000.

Figure 47:
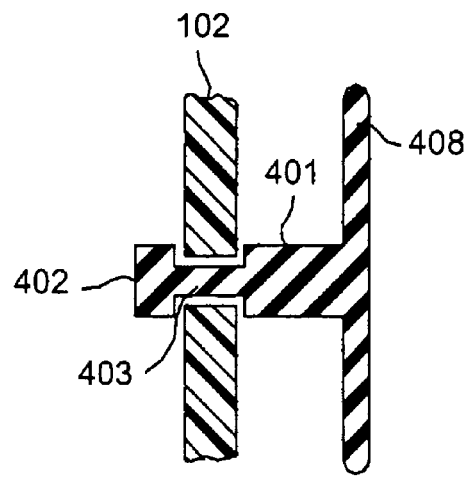
FIG. 47 is a cross-sectional view of another embodiment of a forehead pad engaged with another embodiment of a forehead support according to the present invention.
Figure 48:
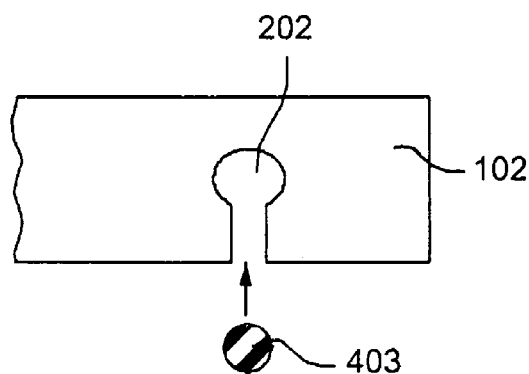
FIG. 48 is a top view of the embodiment of the forehead pad and the embodiment of the forehead support shown in FIG. 47.
Figure 49:
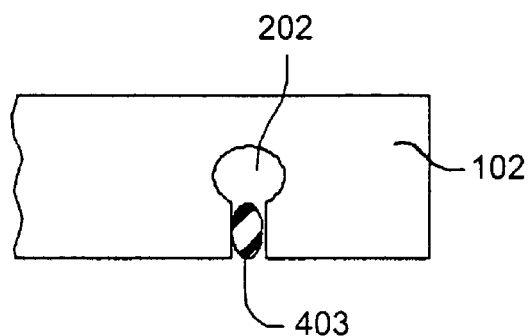
FIG. 49 is a top view of the embodiment of the forehead pad engaged with the embodiment of the forehead support shown in FIG. 47 during an intermediate assembly step.
Figure 50:
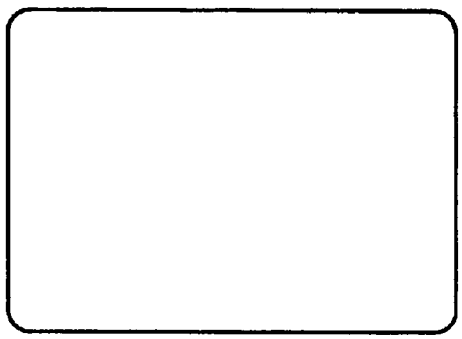
FIG. 50 is a front view of a prior art forehead pad.
Figure 51:
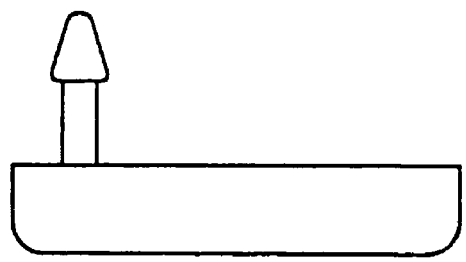
FIG. 51 is a top view of the forehead pad shown in FIG. 50.
Figure 52:
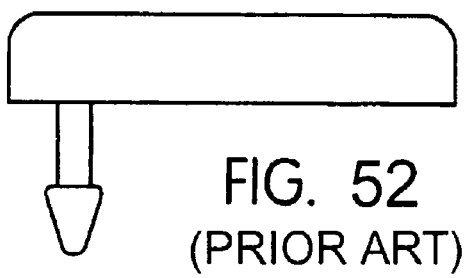
FIG. 52 is bottom side view of the forehead pad shown in FIG. 50.
Figure 53:
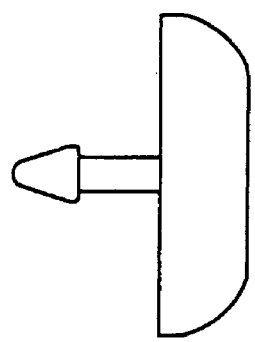
FIG. 53 is a left view of the forehead pad shown in FIG. 50.
Figure 54:
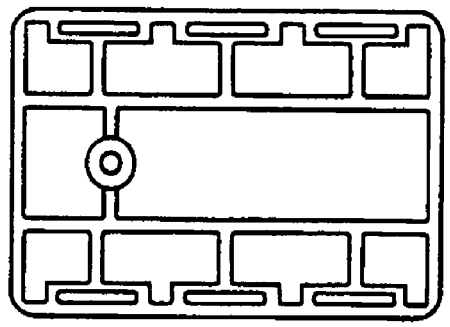
FIG. 54 is a top view of a prior art forehead pad.
Figure 55:
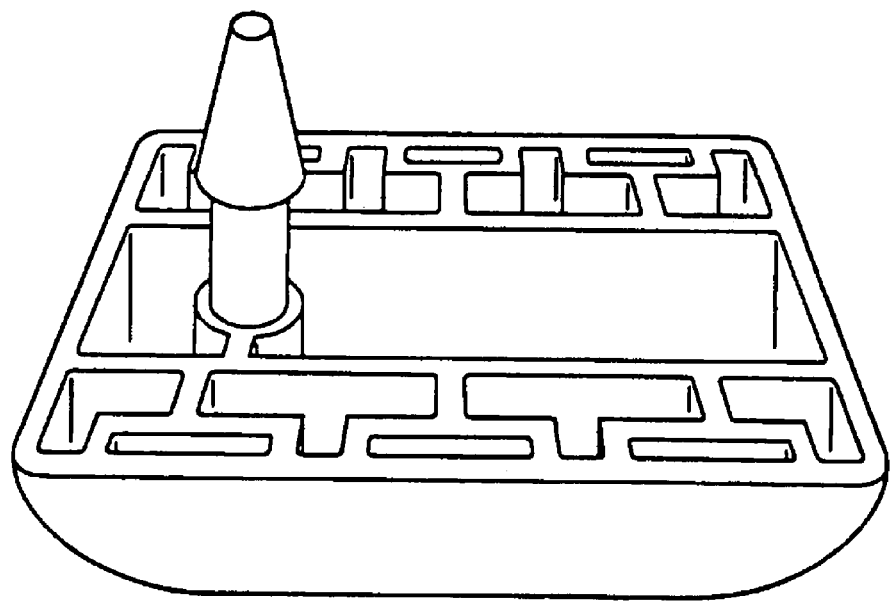
FIG. 55 is a perspective view of the forehead pad shown in FIG. 55.
Figure 56:
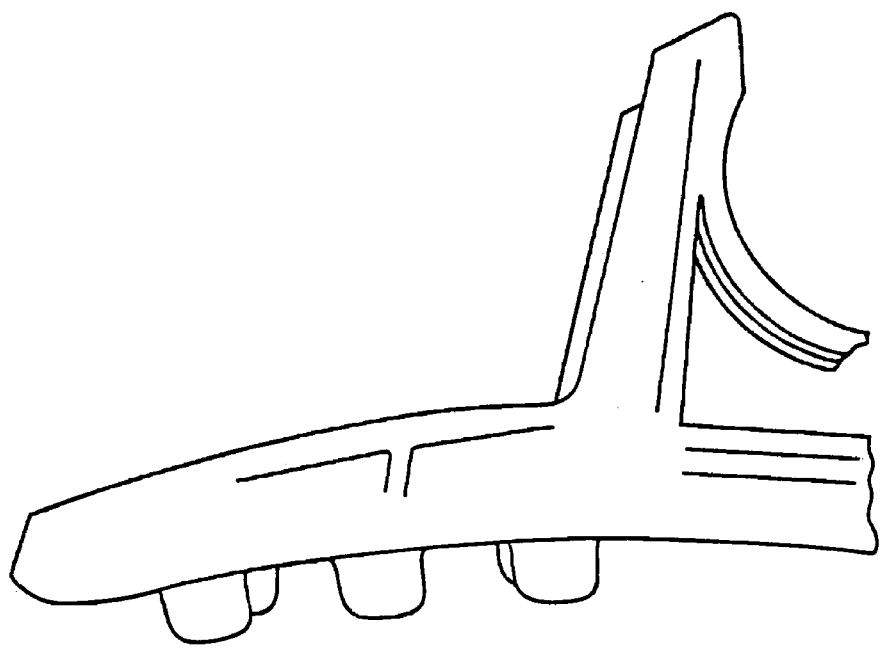
FIG. 56 is a top view of a prior art forehead support.
Figure 57:
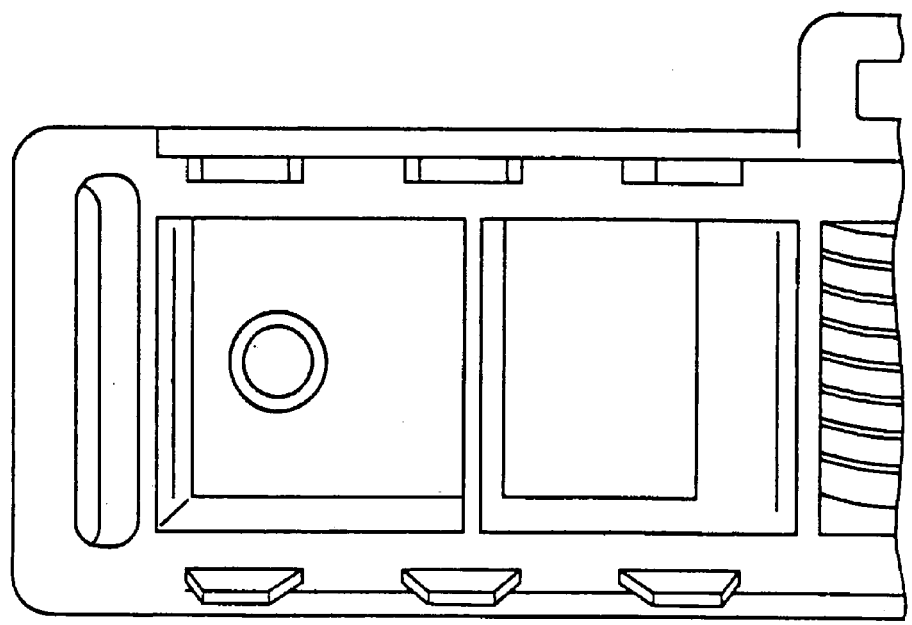
FIG. 57 is a front view of a prior art forehead support.

In another embodiment of the invention, the support post 1010 includes a generally cylindrical end region adapted to engage with a key-shaped slot of a forehead support. To attach the stalk to the forehead support, a small-diameter portion of the end region is slid through a generally rectangular region of smaller diameter, causing it to distort, before being received within a generally cylindrical region having a diameter slightly larger than that of the stalk, as in FIGS. 47 to 49. The smaller diameter portion of the end region defines two shoulder regions, similar in function to those of other embodiments, adapted to prevent axial movement of the pad.

In one form, the base portion 408 of the forehead pad is generally plate- or disc-shaped. In a preferred form, it presents a concave surface to a forehead of a patient in use. Possible shapes of the base portion include rectangular and oval shapes.

The shape of the support post 401 and base portion 408 are designed to cause lines of force 490 to be smoothly and evenly carried from the support post 401 to the base portion 408, as shown in FIG. 58. In this way there is an even distribution of pressure across the user's forehead 813. The lines of force 490 are not concentrated. The support post 401 is of a design to be sufficiently rigid so that it does not buckle when inserted and pushed.

An alternative embodiment of a forehead pad according to the present invention is shown in FIGS. 59 to 62. In this embodiment, there is a "cleat" on the T-bar arm of the forehead support, the cleat having a generally oval shape and positioned away from the surface of the arm of the forehead support, defining a space between the front side of the cleat and the arm of the forehead support. The pad has a generally oval shape, defining a major and minor axis and includes a shaft therethrough with a varying profile. The initial profile is of a complementary shape to the cleat, allowing the pad to fit on the cleat. Further along the shaft, the profile rotates approximately 90°, defining a shoulder region. In this way, the pad can be inserted over the cleat and then twisted approximately 90° to lock it in position. In this position, the shoulder region of the pad engages with the front side of the cleat.

In a preferred embodiment, the pad includes a pair of dimples adapted to engage with corresponding protrusions on the arm of the forehead support. Engagement between the dimples and respective protrusions provides feedback to the user that the pad has been correctly rotationally aligned. Furthermore, the engagement between dimples and protrusions reduces unintentional rotational movement of the pads. Alternative locking mechanisms, such as those with keys or moveable slider blocks, fall within the scope of the invention.

Figure 63:
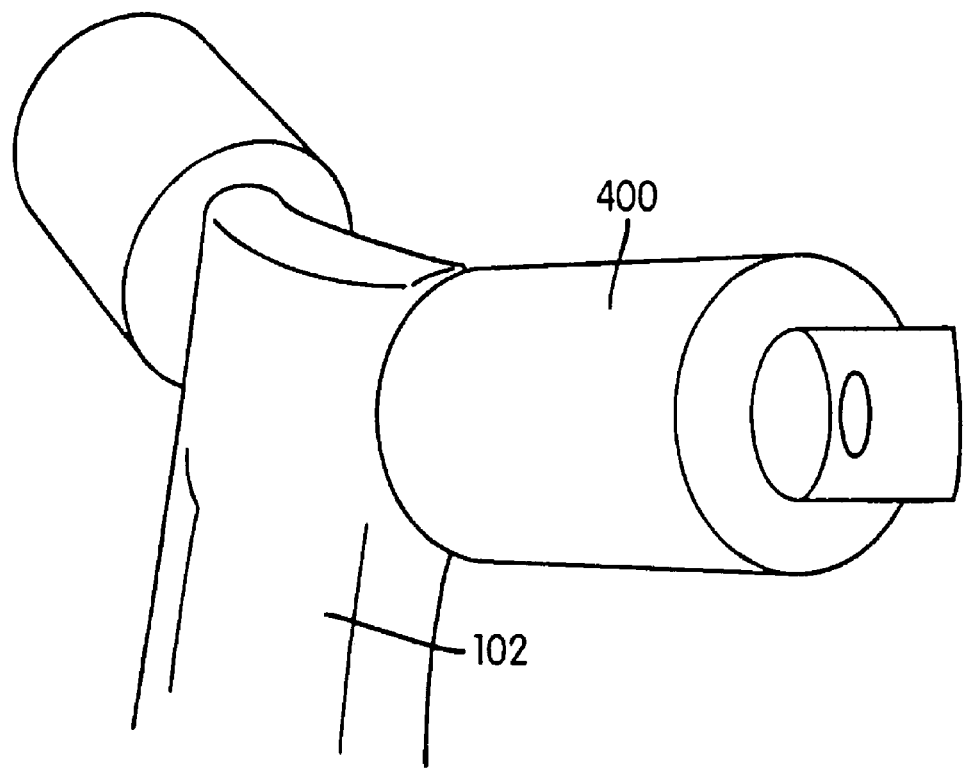
FIG. 63 is a perspective view of another embodiment of a forehead pad according to the present invention.

FIG. 63 shows an alternative embodiment of the invention. In this embodiment, the arms of the forehead support 102 are generally cylindrical and are covered in a generally cylindrical "pipe" of foam, forming the forehead pad 400. Because of the generally constant radius of the forehead arm and the pipe, there are no sharp edges presented to the forehead of the user, regardless of the angle of the support with respect to the forehead. In one form, the foam only partly surrounds the arm of the forehead support. Furthermore, because of the generally constant properties of the foam with respect to angular position, the lines of force are smoothly carried to the forehead of the user. In another embodiment, the pipe is shaped so that its outer surface positions a thicker section at the forehead and the bore through the pipe need not be circular, permitting attachment to non-circular arms.

Figure 64:
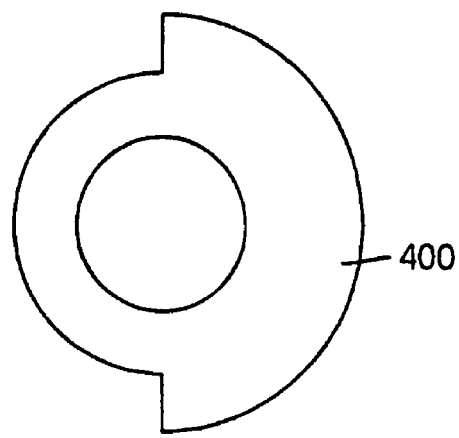
FIG. 64 is a cross-sectional view of another embodiment of a forehead pad according to the present invention.
Figure 65:
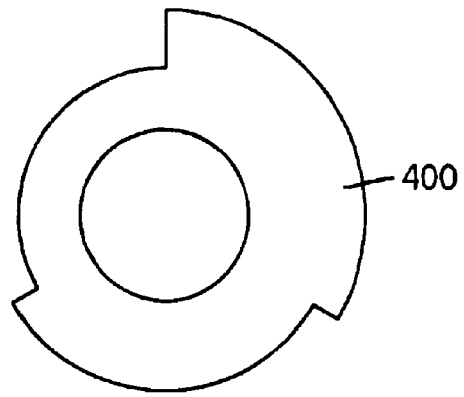
FIG. 65 is a cross-sectional view of another embodiment of a forehead pad according to the present invention.
Figure 66:
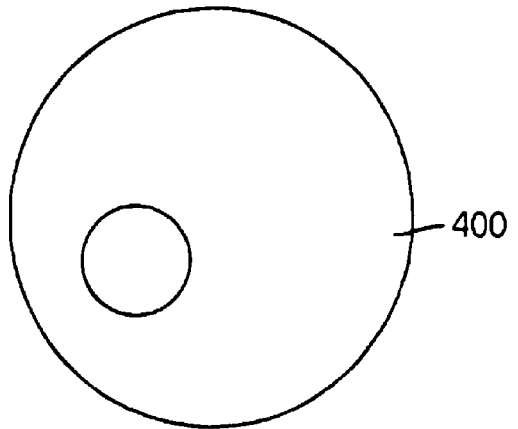
FIG. 66 is a cross-sectional view of another embodiment of a forehead pad according to the present invention.

In alternative embodiments, shown in FIGS. 64 to 66, the thickness of the pipe about a circumference can be varied to provide adjustability. The pipe can have two sections of different thicknesses (FIG. 64), three sections of different thickness (FIG. 65), or can have an eccentric thickness (FIG. 66). These embodiments offer several other advantages including increasing the snugness of the fit without removal of the mask, decreasing tightness of the pipe and associated symptoms, e.g., sweating and discomfort, without removal of the mask.

Figure 67:
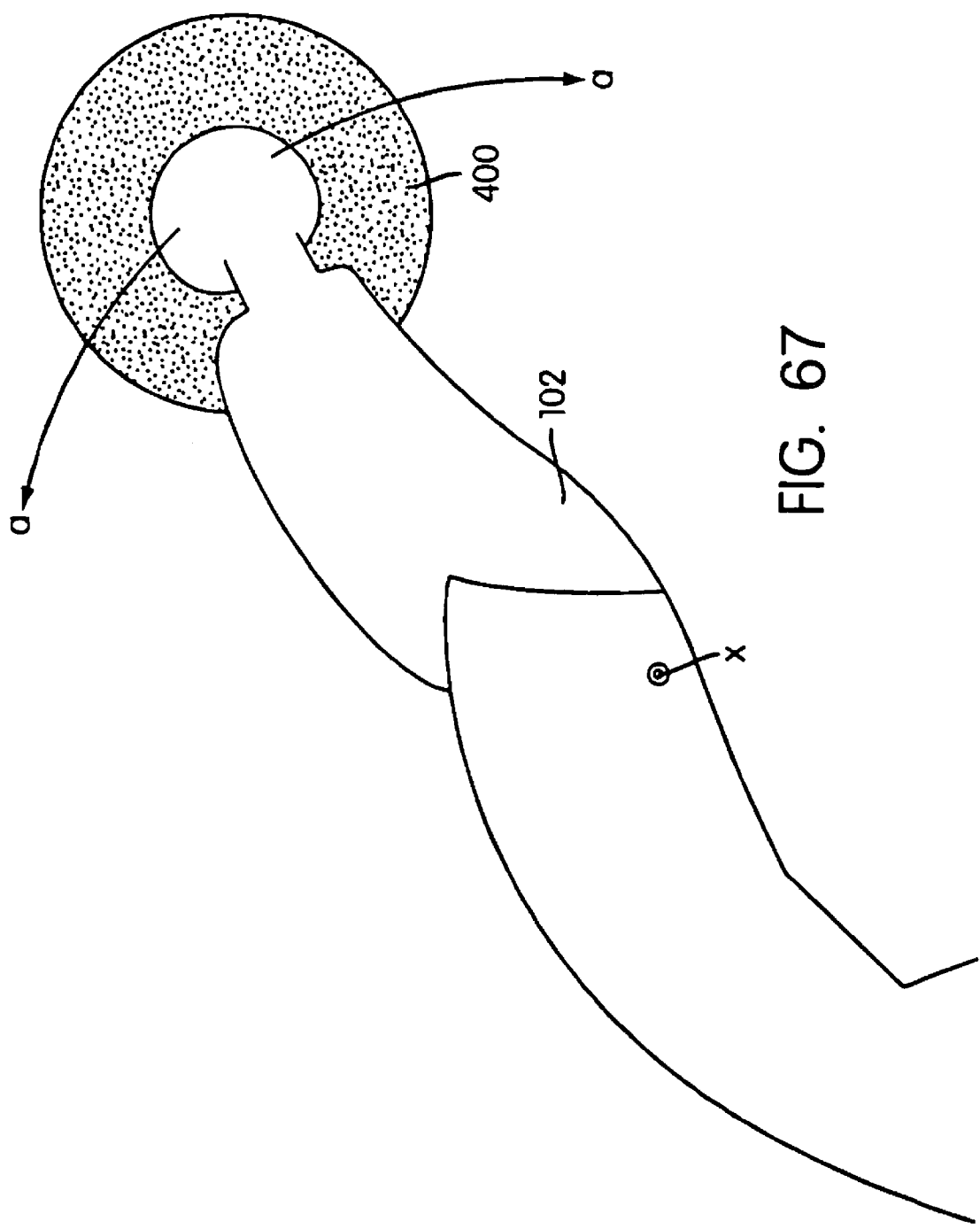
FIG. 67 is a partial cross-sectional view another embodiment of a forehead pad according to the present invention.
Figure 68:
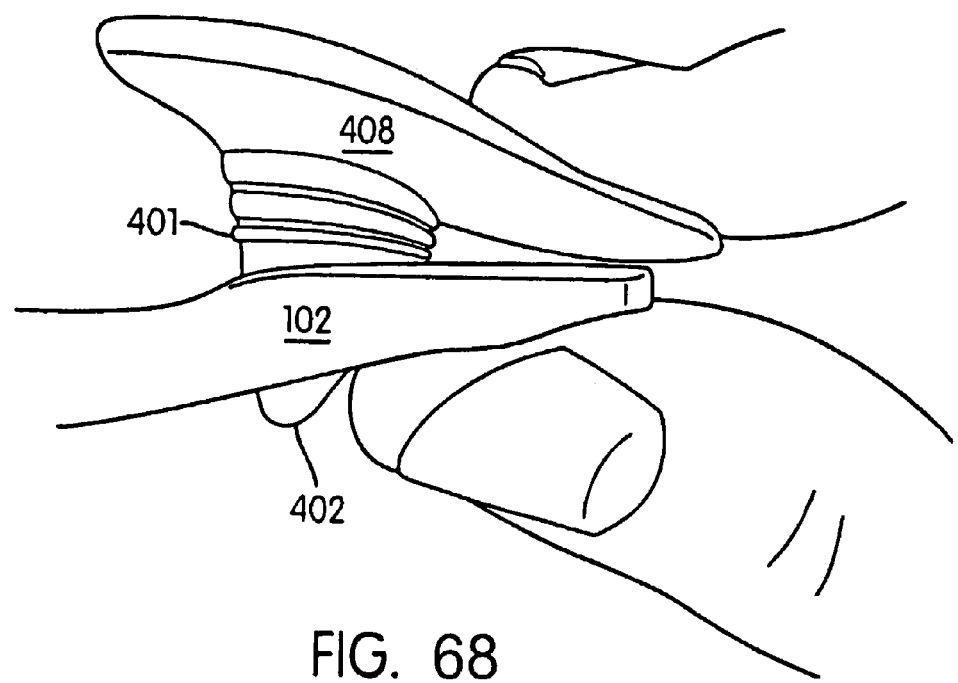
FIG. 68 shows an embodiment of a forehead pad according to the present invention flexed in a first direction.
Figure 69:
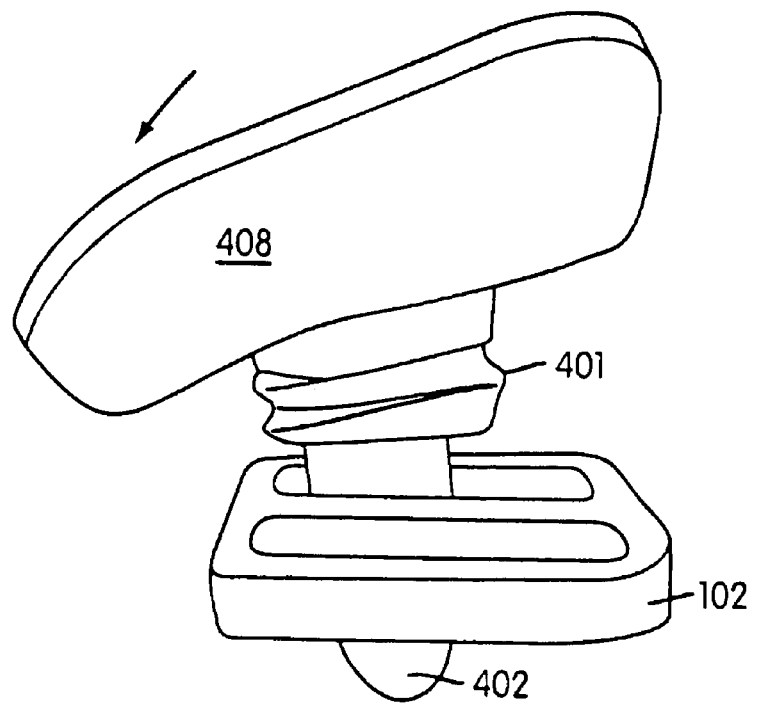
FIG. 69 shows an embodiment of a forehead pad according to the present invention flexed in a second direction.
Figure 70:
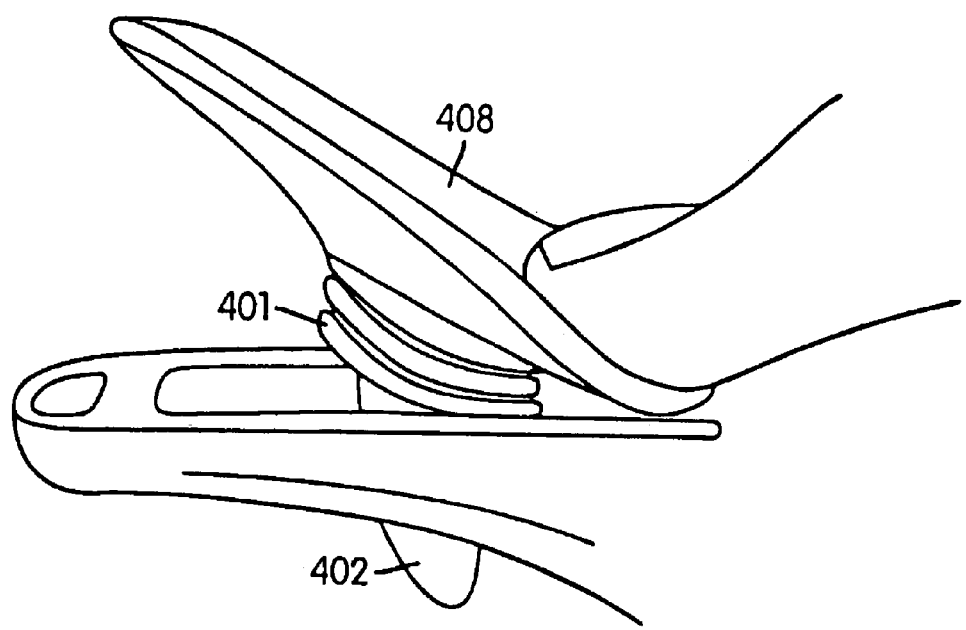
FIG. 70 shows an embodiment of a forehead pad according to the present invention flexed in a third direction.
Figure 71:
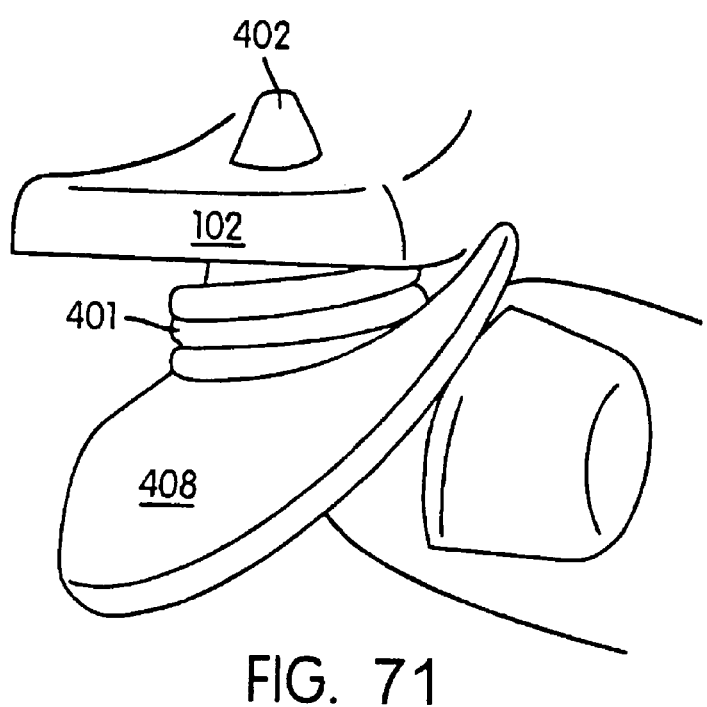
FIG. 71 shows an embodiment of a forehead pad according to the present invention flexed in a fourth direction.

FIG. 67 shows an alternative embodiment of the invention. In this embodiment, the tip of the forehead support 102 comprises a generally spherical ball. A foam or silicone pad 400, also generally spherically shaped, is placed over the tip of the forehead support 102. The general spherical shape smoothly carries lines of force from the tip of the forehead support to the forehead, regardless of orientation. In this way there is an even distribution of force on the forehead of the user.

While this application has described a few embodiments of forehead pads and forehead supports, it is well understood by one skilled in the art that various forehead pads, forehead supports, and masks can be used interchangeably. A type of forehead pad is not limited to a particular forehead support or to a specific mask.

In an alternative embodiment, the support post of the forehead pad can be used in combination with an extruded pad such as used on the MIRAGE mask (U.S. Pat. No. 6,119,693). Another embodiment has a forehead pad devoid of a convex surface, instead including a support post used in combination with a concave surface. Another embodiment includes a pad with varying cross-sectional thicknesses, e.g., it could be thinner at edges for greater flexibility when rolling, than at the center.

It can thus be appreciated that the aspects of the present invention have been fully and effectively accomplished. The foregoing specific embodiments have been provided to illustrate structural and functional principles of the present invention, and are not intended to be limiting. To the contrary, the present invention is intended to encompass all modifications, alterations and substitutions within the spirit and scope of the present invention.

What is claimed is:

1. A forehead pad comprising:
   a) a base portion, wherein the base portion defines
      (i) a first surface, and
      (ii) a second surface to contact a user's forehead;
   b) a support post, wherein the support post projects from the first surface and comprises
      (i) a cut away portion defining an undercut between the cut away portion and the base portion, the cut away portion having a first diameter,
      (ii) a generally cylindrical portion extending from the cut away portion, the generally cylindrical portion having a second diameter smaller than the first diameter, and
      (iii) a necked down region extending from the generally cylindrical portion, the necked down region having a third diameter smaller than the second diameter; and
   c) a head adapted to connect the support post to a forehead support of a respiratory mask, the head having a base connected to the support post and having a tapered shape.

2. A forehead pad according to claim 1, wherein the generally cylindrical portion extends from the cut away portion at an angle defined between a tangent to the first surface at a point of contact between the support post and the base portion that is less than about 90°.

3. A forehead pad according to claim 2, wherein the angle is between about 65° and 80°.

4. A forehead pad according to claim 1, further comprising: a hollowed out region extending from the second surface a pre-determined distance into the support post.

5. A forehead pad according to claim 4, wherein the hollowed out region extends into the generally cylindrical portion of the support post.

6. A forehead pad according to claim 4, wherein the hollowed out region is cylindrical.

7. A forehead pad according to claim 1, wherein the base portion, the support post, and the head are integrally formed as one piece.

8. A forehead pad according to claim 7, wherein the base portion, the support post, and the head are molded.

9. A forehead pad according to claim 7, wherein the forehead pad is formed of flexible material.

10. A forehead pad according to claim 1, wherein the undercut is triangular.

11. A forehead pad according to claim 1, wherein the second surface is concave relative to the user.

12. A forehead pad according to claim 1, wherein the necked down region is tapered.

13. A forehead pad according to claim 1, wherein the base of the head defines a lip between the head and the support post.

14. A forehead pad according to claim 1, wherein the head is bullet shaped.

15. A forehead pad according to claim 1, wherein the head comprises a rounded end opposite the base.

16. A forehead pad according to claim 1, wherein the support post is axially compressible.

17. A forehead pad assembly, comprising:
    two forehead pads according to claim 1; and
    a connector that connects the base portions of the two forehead pads.

18. A forehead pad assembly according to claim 17, wherein the two forehead pads and the connector are integrally formed as one piece.

19. A forehead pad assembly according to claim 18, wherein the two forehead pads and the connector are molded.

20. A forehead support assembly for a respiratory mask, comprising:
    a forehead support comprising two apertures; and
    a forehead pad assembly according to claim 17, wherein the forehead pad assembly is repeatably attachable to and detachable from the forehead support assembly by inserting a respective support post of a respective forehead pad into a respective aperture of the forehead support to attach the forehead pad assembly and removing each respective support post from each respective aperture to detach the forehead pad assembly.

21. A forehead support assembly according to claim 20, wherein each head of the forehead pad assembly is adapted to be attached to the forehead support using a push-on motion.

22. A forehead support assembly according to claim 20, wherein each head is adapted to provide an audible sound upon successful insertion into a respective aperture of the forehead support.

23. A forehead support assembly according to claim 20, wherein the support posts and support are structured such that an attachment force to attach the forehead pad assembly and the forehead support is less than a detachment force to detach the forehead pad assembly from the forehead support.

24. A forehead support assembly according to claim 20, wherein the support post is sufficiently rigid to distribute lines of force from the forehead support evenly across the second surface of the forehead pad.

25. A forehead support assembly according to claim 24, wherein the support post and the base portion are configured to evenly distribute forces across the second surface without localized pressure points.

26. A respiratory mask assembly comprising the forehead support assembly of claim 20.

27. A respiratory mask assembly according to claim 26, wherein the forehead support is adjustably connected to the respiratory mask assembly.

* * * * *